United States Patent
Takemoto et al.

(10) Patent No.: US 7,067,533 B2
(45) Date of Patent: *Jun. 27, 2006

(54) AMINOPHENOXYACETAMIDE DERIVATIVES AND PHARMACEUTICAL COMPOSITION CONTAINING THEREOF

(75) Inventors: Naohiro Takemoto, Osaka (JP); Hirokazu Annoura, Kyoto (JP); Norihito Murayama, Osaka (JP)

(73) Assignee: Daiichi Asubio Pharma Co., Ltd., Tokyo (JP)

( * ) Notice: Subject to any disclaimer, the term of this patent is extended or adjusted under 35 U.S.C. 154(b) by 378 days.

This patent is subject to a terminal disclaimer.

(21) Appl. No.: 10/009,566

(22) PCT Filed: Apr. 13, 2001

(86) PCT No.: PCT/JP01/03198

§ 371 (c)(1),
(2), (4) Date: Dec. 12, 2001

(87) PCT Pub. No.: WO01/79170

PCT Pub. Date: Oct. 25, 2001

(65) Prior Publication Data
US 2003/0139447 A1 Jul. 24, 2003

(30) Foreign Application Priority Data
Apr. 13, 2000 (JP) ............... 2000-112100

(51) Int. Cl.
| A61K 31/4468 | (2006.01) |
| A61K 31/4523 | (2006.01) |
| A61K 31/454 | (2006.01) |
| A61K 31/4545 | (2006.01) |
| C07D 211/58 | (2006.01) |
| C07D 215/00 | (2006.01) |
| C07D 217/00 | (2006.01) |

(52) U.S. Cl. ............ 514/317; 514/235.5; 514/307; 514/314; 514/318; 514/323; 514/331; 546/144; 546/146; 546/153; 546/168; 546/192; 546/193; 546/196; 546/207; 546/208; 546/224; 544/129

(58) Field of Classification Search ......... 546/193, 546/192, 201, 146, 144; 514/318, 323, 331, 514/314, 307, 237.2; 544/129
See application file for complete search history.

(56) References Cited

U.S. PATENT DOCUMENTS 6,559,146 B1 * 5/2003 Annoura et al. ......... 514/237.2

FOREIGN PATENT DOCUMENTS
| EP | 0 982 026 A | 3/2000 |
| WO | WO 00 23076 A | 4/2000 |

OTHER PUBLICATIONS

Bouillon et al., "Antagonistic activity of 24-oxa-analogs of vitamin D," *Steriods: Structure, Function, and Regulation*, 1995, pp. 484-490, vol. 60, Elsevier Science Publishers, New York, New York, USA.

McMahon et al., "Calbindin-$D_{28k}$ buffers intracellular calcium and promotes resistance to degeneration in PC12 cells", *Molecular Brain Research*, 1998, 54:56-63.

Ng et al., "The neurotoxin MPTP increases calbindin-$D_{28k}$ levels in mouse midbrain dopaminergic neurons", *Molecular Brain Research*, 1996, 36:329-336.

Masumura et al., "Selective induction of fibroblast growth fact or receptor-1 mRNA after transient focal ischemia in the cerebral cortex of rats", *Neuroscience Letters*, 1996, 213:119-122.

\* cited by examiner

*Primary Examiner*—Kamal A. Saeed
*Assistant Examiner*—Janet L. Coppins

(57) ABSTRACT

The present invention relates to an aminophenoxyacetamide derivative of the formula (I):

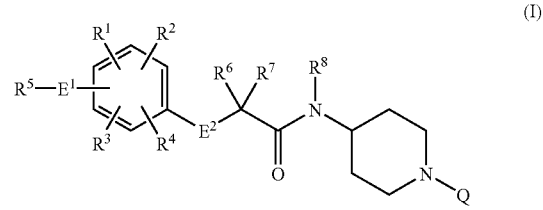

wherein $R^1$ to $R^4$ are, independent from each other, a hydrogen atom or an optionally substituted alkyl group; $E^1$ is —$NR^4$—; and $E^2$ is an oxygen atom or —$NR^{10}$—; Q is the group —X—Y-Q', wherein X and Y are connecting bonds or X is an alkylene or alkenylene group and Y is selected from a group comprising C=O, NHC(=), and C(=O)NH, and Q' is a hydrogen atom or a phenyl or pyridyl group which may be substituted; and pharmaceutically acceptable salts thereof. The present invention further relates to compositions comprising compounds of the formula (I) and methods of using said compounds for treating cerebral functional disorders and cerebral organic disorders.

8 Claims, 1 Drawing Sheet

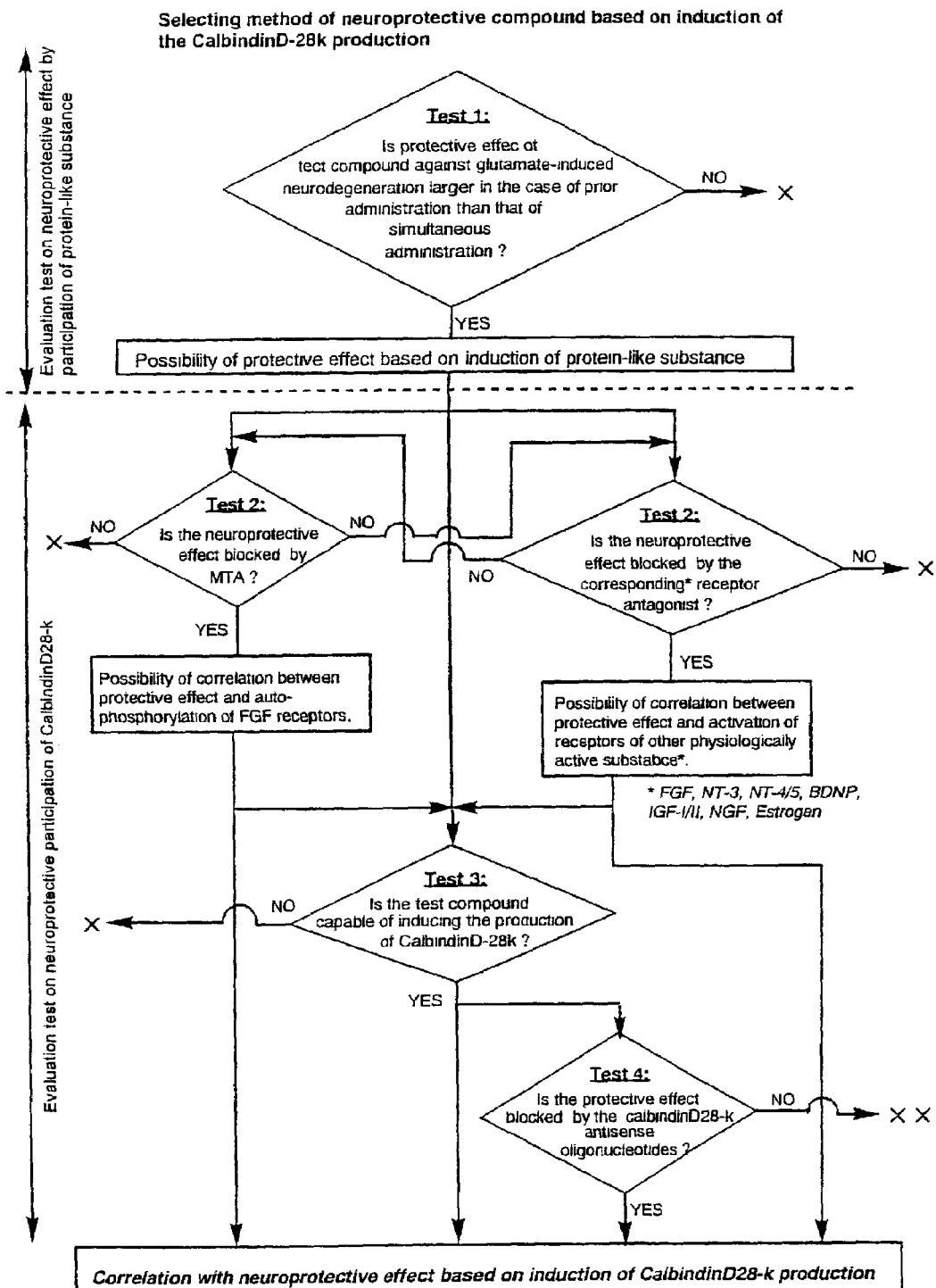

AMINOPHENOXYACETAMIDE DERIVATIVES AND PHARMACEUTICAL COMPOSITION CONTAINING THEREOF

TECHNICAL FIELD

The present invention relates to cerebral functional or organic disorders improving and treating agents containing aminophenoxyacetamide derivatives and pharmaceutically acceptable salt thereof as an active ingredient, having neuroprotective effect by inducing the production of CalbindinD-28k, one of $Ca^{2+}$-binding proteins, and to the methods for selecting these neuroprotective aminophenoxyacetamide derivatives. More specifically, the present invention relates to the therapeutic and improving agents for various cerebral dysfunction due to various ischemic disorders such as cerebral infarction, intracerebral hemorrhage and cerebral arteriosclerosis. Furthermore, the present invention relates to therapeutic and improving agents for various cerebral organic disorders due to senile dementia, sequelae of cerebral injury, or surgical operation, Alzheimer's disease, Parkinson's disease, and amyotrophic lateral sclerosis, and Huntington's disease, etc.

BACKGROUND ART

It is considered that the progressive and delayed death of nerve cells, observed in cerebral injury and cerebrovascular disease such as intracerebral hemorrhage, transient cerebral ischemia, and cerebral infarction, is mainly caused by the increase of the intracellular $Ca^{2+}$ concentration, the various factors of which are related to signal transduction to cause, for example, the abnormal activation of receptors by over releasing glutamate which is internal excitability, the activation of ion channels, and the induction of reactive oxygen species/free radicals. [F. B. Meyer, *Brain Res. Rev.,* 14, 227 (1989); E. Boddeke et al., *Trends Pharmacol. Sci.,* 10, 397 (1989); J. M. McCall et al., *Ann. Rep. Med. Chem.,* 27, 31 (1992)].

From these points of view, antagonists for glutamate receptors, calcium channel blockers antioxidants and so on have been applied for medicaments of preventing or suppressing the neurodegeneration. However, these clinically used medicaments suppress only a few pathways relating to the increase of the cellular $Ca^{2+}$ concentration, and therefore are not yet sufficient enough for preventing or suppressing the neurodegeneration.

On the contrary, the internal production of CalbindinD-28k is induced by activation of receptors for many physiologically active substance's such as FGF, LT-3, NT-4/5, BDNF, IGF-I/II, PDGF, estrogen and so on, and as well as by activation of FGF receptor, which is one of nerve growth factor receptors [C. V.-Abejon et el., *Neuron,* 15, 105 (1995); A. Silva et al., *Brain Res. Bull.,* 1, 35 (2000)]. And CalbindinD-28k, one of $Ca^{2+}$-binding proteins and mainly distributed in vulnerable site against ischemic disorders in the central nervous system, which is known to show buffer action against the increase of intracellular $Ca^{2+}$ concentration. [A. M. Lacopino et al., *Neurodegeneration,* 3, 1 (1994); M. P. Mattson et al., *Neuron,* 6, 41 (1991)]

Accordingly, it is expected to achieve sufficient neuroprotective effects against the increase of intracellular $Ca^{2+}$ concentration caused by any kinds of pathways if CalbindinD-28k, one of the $Ca^{2+}$-binding proteins per se, can be supplied in a cell. Namely, it is expected that medicaments containing CalbindinD-28k would be extremely effective therapeutic and improving agents against cerebral functional and due to various ischemic disorders such as cerebral infarction, intracerebral hemorrhage and cerebral arteriosclerosis. It is also expected to be effective against cerebral dysfunction due to cerebral ischemic disorders due to sequelae of senile dementia, cerebral injury and surgical operation, Alzheimer's disease, Parkinson's disease, amyotrophic lateral sclerosis and so on.

However, it is very difficult and therefore it is not likely to administer the CalbindinD-28k protein directly into the desirable site in the central nervous system of a body in view of the limitations existing in the pharmacological and pharmaceutical methodology because CalbindinD-28k itself is an unstable macro molecular weight protein having 28 Kd (Kilo Dalton) of molecular weight.

On the other hand, the lower molecular weight compounds capable of inducing the production of CalbindinD-28k protein can be easily prepared into the various kinds of pharmaceutical compositions by the conventional technique. Therefore, these lower molecular weight compounds would induce the production of the neuroprotective CalbindinD-28k protein once easily administered into a body, showing the buffering action against the increase of the intracellular $Ca^{2+}$ concentration. That is, these lower molecular weight compounds can be effective pharmaceutical compounds for improving and treating cerebral functional and organic disorders.

Under these circumstances, one objective of the present invention is to select and to provide the lower molecular-weight neuroprotective compounds capable of inducing the production of CalbindinD-28k, one kind of $Ca^{2+}$-binding proteins, via phosphorylation of receptors of various physiologically active substances, as well as to provide the pharmaceutical compositions of low toxicity in suitable preparations such as intravenous injectable solution.

The other objective of the present invention is to provide the therapeutic and improving agents for cerebral functional disorders due to various ischemic disorders such as cerebral infarction, intracerebral hemorrhage and cerebral arteriosclerosis, as well as cerebral organic disorders such as sequelae of senile dementia, cerebral injury. or surgical operation, Alzheimer's disease, Parkinson's disease and amyotrophic lateral sclerosis.

DISCLOSURE OF THE INVENTION

As one aspect of the present invention, it is provided aminophenoxyacetamide derivatives represented by the following formula (I):

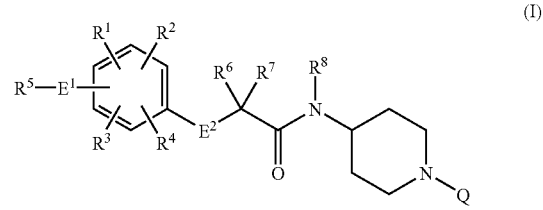

wherein, $R^1$, $R^2$, $R^3$ and $R^4$ are, independent from each other, hydrogen atom or lower alkyl group which may be substituted;

$R^5$, $R^6$, $R^7$ and $R^8$ are, independent from each other, hydrogen atom or lower alkyl group which may be substituted;

$E^1$ is group —$NR^9$ (in which, $R^9$ is hydrogen atom or alkyl group which may be substituted);

$E^2$ is oxygen atom or group —$NR^{10}$ (in which, $R^{10}$ is hydrogen atom; alkyl group which may be substituted; aryl group which may be substituted or aralkyl group which may be substituted); Q is a group of —X—Y-Q', in which X is a connecting bond, lower alkyl group, lower alkenyl group or lower alkynyl group; Y is a connecting bond, or a group selected from the groups consisting of C=O, C(=O)NH, NHC(=O), —O—, —S—, CH(OH), —O—CH(OH), and —O—CH2—CH(OH), in which hydrogen atom of amido group may be substituted with lower alkyl group; and Q' is hydrogen atom or a cyclic group selected from the groups consisting of aryl group, heteroaryl group, saturated or unsaturated cyclic hydrocarbon group, and satuated or unsaturated heterocyclic group, wherein one or more of the hydrogen atom in the cylclic group of Q' may be substituted;

provided that X and Y are both connecting bond then Q' is not hydrogen atom; or provided that one of X and Y is other than connecting bond then E2 is the group —O— and all of the groups of R1, R2, R3 and R4 are not hydrogen atom; or a pharmaceutically acceptable salt thereof.

In the description of a lower alkyl group may be specifically a straight or branched alkyl group or the number of carbon atoms from $C_1$ to $C_6$, for example, methyl, ethyl, n-propyl isopropyl and so on and more preferably, methyl or ethyl. In the description of lower alkenyl group may be specifically $C_1$ to $C_6$ alkenyl group, and lower alkynyl may be specifically $C_1$ to $C_6$ alkynyl group.

Furthermore, the present invention provides the aminophenoxyacetamide derivatives of the formula (I), in which;

$R^1$, $R^2$, $R^3$ and $R^4$ all are methyl group;

when $E^1$ is oxygen atom; $E^2$ is the group —$NR^9$ (in which, $R^9$ is hydrogen atom; alkyl group which may be substituted; aryl group which may be substituted or aralkyl group which may be substituted); or when $E^1$ is group —$NR^{10}$ (in which, $R^{10}$ is hydrogen atom; alkyl group which may be substituted; aryl group which may be substituted; or aralkyl group which may be substituted); $E^2$ is oxygen atom;

$R^5$, $R^6$, $R^7$ and $R^8$ are, independent from each other, hydrogen atom or lower alkyl group;

Q is group —X—Y-Q' (in which, Q' is hydrogen atom, phenyl group which may be substituted, pyridyl group which may be substituted, quinolyl group which may be substituted, isoquinolyl group which may be substituted; benzothiazole group which may be substituted or benzimidazole group which may be substituted; or pharmaceutically acceptable salts thereof.

More specifically, the following compound groups (1) to (4) are the specific embodiments of the aminophenoxyacetamide derivatives of the formula (I) of the present invention having the excellent effect.

(1) The aminophenoxyacetamide derivatives claimed claim 1, wherein;

$R^1$, $R^2$, $R^3$ and $R^4$ are, independent from each other, hydrogen atom; or alkyl group which may be substituted;

$R^5$ is hydrogen atom or alkyl group which may be substituted; $E^1$ is —NH—;

$E^2$ is oxygen atom; or pharmaceutically acceptable salts thereof.

(2) The aminophenoxyacetamide derivatives claimed in claim 1, wherein;

$R^1$, $R^2{}_1$, $R^3$ and $R^4$ are, independent from each other, hydrogen atom; or alkyl group which may be substituted;

$R^5$ is hydrogen atom or alkyl group which may be substituted;

$E^1$ and $E^2$ are —NH—; or pharmaceutically acceptable salts thereof.

(3) The aminophenoxyacetamide derivatives claimed in claim 2, wherein;

$R^5$ is hydrogen atom or alkyl group which may be substituted;

$E^1$ is —NH—;

$E^2$ is oxygen atom;

when X is connecting bond, Y is —CONH—; or when X is —CONH—, Y is connecting bond;

Q' is phenyl group which may be substituted; or pharmaceutically acceptable salts thereof.

(4) The aminophenoxyacetamide derivatives claimed in claim 2, wherein;

$R^5$ is hydrogen atom or alkyl group which may be substituted;

$E^1$ is —NH—;

$E^2$ is oxygen atom;

X is connecting bound or alkylene group and Y is one of the groups consisting of —CH(OH)—, —O—CH(OH)—, and —O—CH$_2$—CH(OH)—;

Q' is phenyl group which may be substituted; or pharmaceutically acceptable salts thereof.

According to the present inventor's investigations, it is confirmed that the aminophenoxyacetamide derivatives represented by the formula (I) effectively induced the production of CalbindinD-28K in low concentration and possessed excellent neuroprotective effect. Further, these compounds are also confirmed to have high safety margin, and are suitable for preparation of various kinds of pharmaceutical compositions.

Therefore, as a further embodiment, the present invention provides an improving and therapeutic agent for the cerebral functional and organic disorders containing aminophenoxyacetamide derivatives represented by the formula (I) or pharmaceutically acceptable salt thereof, as an active ingredient.

As another embodiment, the present invention provides effective and simple method of selecting (screening) lower molecular weight compounds capable of inducing the production of the CalbindinD-28k, one of $Ca^{2+}$-binding proteins.

The method of selecting low molecular weight compounds consists of several evaluation tests mentioned below;

(1) Evaluation test to compare the neuroprotective effect of the test compounds against glutamate-induced neurodegeneration, between the administration thereof prior to the glutamate addition and the simultaneous administration thereof.

(2) The test to confirm whether or not the aforementioned neuroprotective effect is neuroprotective through phosphorylation of receptors for various physiologically active substances. These tests are conducted by the antagonistic effect of the inhibitors for each of the receptors such as FGF NT-3, NT-4/5, BDNF, IGF-I/II, PDGF, or estrogen, and MTA (5-Deoxy-5-Methylthioadenosine), which specifically inhibits autophosphorylation of FGF receptor.

(3) Evaluation test of inducing capability for each test compounds to produce CalbindinD-28k.

(4) Confirmation test for neuroprotective effect of CalbindinD-28k by the inhibition using its antisense oligonucleotide.

By the above stated evaluation tests, effective compounds having the following features can be selected.

Evaluation Test (1)

This test is to evaluate whether the test compounds have neuroprotective effect against glutamate induced neurodegeneration, by administrating such testing compounds before or simultaneously along with the glutamate to induce the neuronal cell injury.

If the test compound shows greater neuroprotective effect against neurodegeneration induced by glutamate administration in case of pre-treatment than that in case of simultaneously treatment, then the compound may possess effect of inducing protein like substance, which shows neuroprotective effect. Therefore, the compound possessing neuroprotective effect based on the protein like substance induced, including CalbindinD-28k, one of $Ca^{2+}$-binding proteins, is selected by this evaluation test.

Evaluation Test (2)

In the case where neuroprotective effect disappears by the administration of inhibitors to receptors such as FGF, NT-3, NT-4/5, BDNF, IGF-I/II, PDGF and estrogen, then it is confirmed that such neuroprotective effect is caused by the activation of these receptors. Furthermore, in the living cell, MTA (5-Deoxy-5-Methylthioadenosine) specifically inhibits autophosphorylation of FGF receptors. Inhibition of neuroprotective activity by the treatment with MTA (specific inhibitor for self-phspholylation of FGF receptors) confirms that such neuroprotective effect involves phosphorylation of FGF receptors. Therefore, this evaluation test would select the compounds which neuroprotective effect is expressed by the activation of receptors of various physiologically active substances and through phosphorylation of FGF receptor.

Evaluation Test (3):

The compound having effect of inducing CalbindinD-28k production would be selected by this evaluation test.

Evaluation Test (4):

It is necessary for the protective protein to be produced via the signal transduction of cells through the phosphorylation of receptors of various physiologically active substances to provide the neuroprotective effect of the compounds, and the CalbindinD-28k is one of that protective proteins. Therefore, with this evaluation test, the compound which has neuroprotective activity due to the CalbindinD-28k production, is inhibited by using CalbindinD-28k antisense. In this test, the compound having neuroprotective effect is confirmed based on the CalbindinD-28k produced.

The present invention provides effective and simple selecting method of lower molecular weight neuroprotective compounds based on CalbindinD-28k production induced, by using all of the evaluation tests, or using the combination of evaluation tests (1) and (2), evaluation tests (1), (2) and (3), evaluation tests (1) and (3) or evaluation tests (1), (3) and (4).

FIG. 1 shows the flow chart of the selecting methods of the present invention to show the overview of selecting method of lower molecular weight compounds possessing neuroprotective effect based on CalbindinD-28k production induced, by combining aforementioned evaluation tests.

In accordance with the selecting methods of the present invention, the compounds specifically described in the description of the present invention is selected as lower molecular weight compounds possessing the inducing effect on the production of CalbindinD-28k, one of $Ca^{2+}$-binding protein. However, these selecting methods can be applied to selecting various compounds possessing neuroprotective effect based on activation of physiologically active substance's receptors and CalbindinD-28k production inducing effect involving autophosphorylation of FGF receptor, and are not limited to the selection of the compounds described in this specification.

BRIEF DESCRIPTION OF DRAWING

FIG. 1 shows the flow chart of the selecting methods of lower molecular weight compounds possessing neuroprotective effect based on production of CalbindinD-28k induced of the present invention.

BEST MODE FOR CARRYING OUT THE INVENTION

The aminophenoxyacetamide derivatives of the present invention include aminophenoxyacetamides, aminoanilinoacetamides, aminothiophenoxyacetamides, oxyanilinoacetamides and thioanilinoacetamides. Therefore, "aminophenoxyacetamide derivatives" in this specification include all the derivatives stated above as long as not stated otherwise.

In the aminophenoxyacetamide derivatives of the formula (I) provided by the present invention with reference to various substitution group of $R^1$ to $R^{10}$, "halogen atom" includes fluorine atom, chlorine atom and bromine atom.

The term "alkoxy group" stands for a straight-chained or branched-chained $C_1$–$C_5$ alkoxy group, and may include, for example, methoxy, ethoxy, n-propoxy, isopropoxy, n-butoxy, sec-butoxy, tert-butoxy and the like.

The term "alkyl group which may be substituted" stands for a straight-chained or branched-chained $C_1$–$C_5$ alkyl group which may be halogen-substituted, and may include, for example, methyl, ethyl, propyl, trifluoromethyl group, and the like.

The "aryl", a part of the term "aryl group which may be substituted", stands for $C_4$–$C_{14}$ aryl group containing at least one hetero atom(s) such as nitrogen and oxygen atom(s). Examples of the preferred aryl group include phenyl, pyridyl and naphthyl. The suitable substituents of said aryl group include halogen atom such as fluorine atom, chlorine atom and bromine atom; hydroxy group; a straight-chained or branched-chained $C_1$–$C_5$ alkoxy group having 1 to 5 carbon atoms such as methoxy group and ethoxy group; and a straight-chained or branched-chained $C_1$–$C_5$ alkyl group which can be substituted by halogen atom such as methyl, ethyl and trifluoromethyl.

The "aralkyl", a part of the term "aralkyl group which may be substituted", stands for $C_5$–$C_{12}$ aralkyl group containing at least one hetero ring atom(s) such as nitrogen and oxygen atom(s). The examples include benzyl, phenethyl, pyridylmethyl, and pyridylethyl.

The suitable substituents of said aralkyl group include halogen atoms such as fluorine atom, chlorine atom and bromine atom; hydroxy group; a straight-chained or branched-chained $C_1$–$C_5$ alkoxy group such as methoxy group and ethoxy group; and a straight-chained or branched-chained $C_1$–$C_5$ alkyl group which can be substituted by halogen atom such as methyl, ethyl and trifluoromethyl.

The "aryl", a part of the term "aryl group which may be substituted" represented as "Q", stands for $C_4$–$C_{14}$ aryl group which may contain at least one hetero atom(s) such as nitrogen and oxygen atom(s). The examples include phenyl, pyridyl and naphthyl. The suitable substituents of said aryl group include halogen atom such as fluorine atom, chlorine atom and bromine atom; hydroxy group; a straight-chained or branched-chained $C_1$–$C_5$ alkoxy group having 1 to 5 carbon atoms such as methoxy group and ethoxy group, and a straight-chained or branched-chained $C_1$–$C_5$ alkyl group which can be substituted by halogen atom such as methyl, ethyl and trifluoromethyl. Furthermore, these substituents may also include a straight-chained or branched-chained $C_1$–$C_5$ alkyl group which may be substituted by halogen atom such as fluorine atom, chlorine atom and bromine atom.

The "alkylene", a part of the term "alkylene group which may be substituted by hydroxyl group", refers to the substituets "X" and "Y", and preferably represents a straight-chained or branched-chained $C_1$–$C_6$ alkylene group such as methylene, methylmethylene, ethylene, trimethylene, tetramethylene, cyclopropylmethylene and the like.

The term "cycloalkylene" preferably stands for $C_3$–$C_6$ cycloalkylene and may include 1,1-cyclopropylene, 1,2-cyclopropylene, 1,1-cyclobutylene, 1,1-cyclopentylene, 1,1-cyclohexylene and the like. Among them 1,1-cyclopropylene ad 1,2-cycloproylene are more preferable.

The "alkenylene", a part of the term "alkenylene group which may be substituted by lower alkyl group", may include $C_2$–$C_4$ alkenylene such as vinylene, and butadiene, and vinylene is preferably used. The lower alkyl group, which is substituent of alkenylene group, may be methyl, ethyl, propyl, isopropyl and the like.

The term "connected bond" with reference to "X" and "Y" means direct bond. Therefore, if "X" and/or "Y" are connected bond, two adjacent substituents of "X" and/or "Y" are connected directly, and these substituents do not exist as "X" and/or "Y".

The suitable substituents represented as "Q'" for "phenyl group which may be substituted", "phenoxy group which may be substituted", "benzoyl group which may be substituted", "pyridyl group which may be substituted", "quinolyl group which may be substituted", "isoquinolyl group which may be substituted", "benzothiazole group which may be substituted" and "benzimidazolyl group which may be substituted", may include halogen atom such as fluorine atom, chlorine atom and bromine atom; hydroxy group; a straight-chained or branched-chained $C_1$–$C_5$ alkoxy group such as methoxy, ethoxy group and so on. Furthermore, these substituents may also include a straight-chained or branched-chained $C_1$–$C_5$ alkyl group which may be substituted by halogen atom such as methyl, ethyl, trifluoromethyl and the like.

It is understood that when the aminophenoxyacetamide derivatives of the formula (I) of the present invention exist in the isomer forms, each isomers per se, as well as the isomeric mixture, shall be included in the compounds of the present invention. Namely, the structural isomers may exist due to the substituents on the benzene ring. Furthermore, optical isomers may exist due to the asymmetric carbon atom of the hydroxy substituted "X" or "Y" of alkylene group. These isomers shall be included within the scope of the compounds of the present invention.

The aminophenoxyacetamide derivatives of the formula (I) include the compounds (Ia), (Ib) (Ic) and (Id) obtained by the synthetic process mentioned latter. For example, these compounds may be prepared by the following.

The compound (IV), obtained by the reaction of the compound (II) with the ester derivative (III), is hydrolyzed to convert into the carboxylic acid derivative (V). Furthermore, the compound (VIII) is obtained by the reaction of the amine derivative (VI) with the compound (VII), and the protecting group of the compound (VIII) is removed to obtain the amine derivative (IX). Then, the obtained compound (V) is converted into amide compound (X) by the condensation reaction with the compound (IX). Further, the protecting group in the compound (X) thus obtained is removed to obtain compound (Ia), the compound of formula (I) in the claim 1 of the present invention (Process 1).

The compound (Ib), the aminophenoxyacetamide derivative of formula (I) in the claim 2 of the present invention, can be obtained by the following. The amide compound (XII) is obtained by condensation reaction of the carboxylic acid derivative (V'), which is obtained in the Process 1, with compound (XI), and the protecting group of the resultant was removed (Process 2).

The compound (Ib), obtained in the Process 2, can be converted to the compound (Ic) by the reaction with the compound (XIII) (Process 3).

Furthermore, the compound (Id) can be obtained by reacting the compound (Ib) with the compound (XIV) (Process 4).

Each process will be further illustrated by the following reaction scheme.

Process 1:

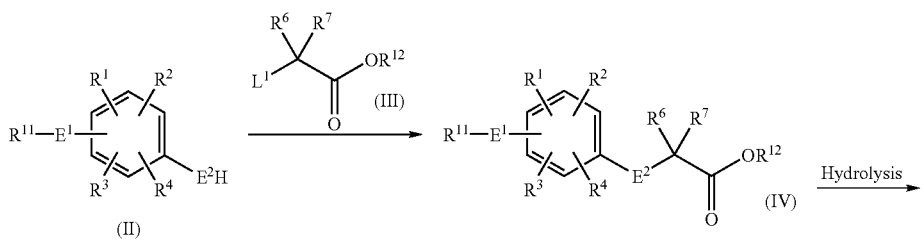

-continued

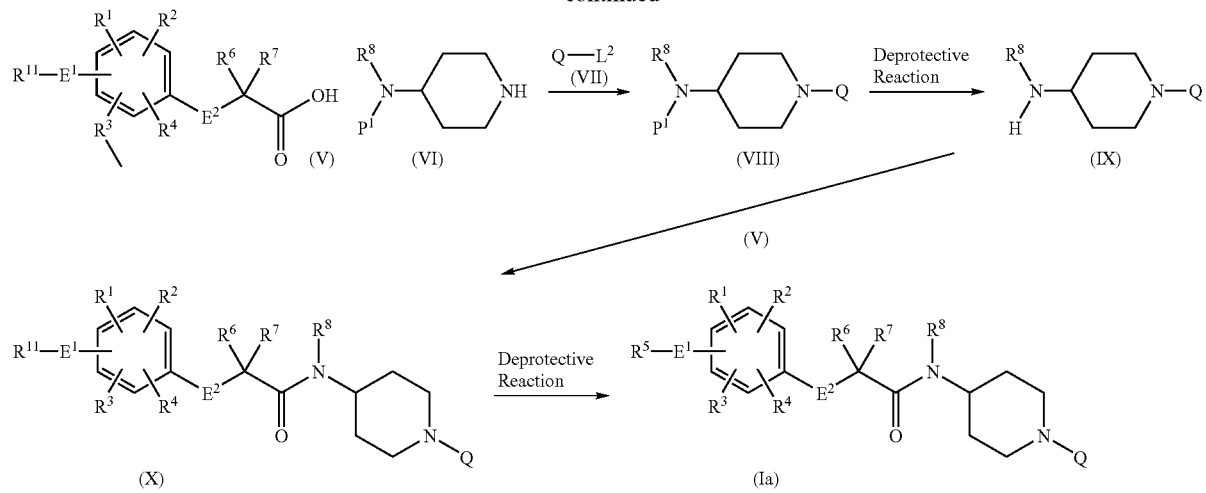

wherein, $R^1$ to $R^8$, $E^1$ and $E^2$ have the same definitions as above; Q has the same meaning as defined in claim 1; and $R^{11}$ is alkyl group which may be substituted, aryl group which may be substituted; aralkyl group which may be substituted; tert-butoxycarbonyl group: ethoxycarbonyl group; acetyl group; benzyloxycarbonyl group; p-methoxybenzyloxycarbonyl group; $R^{12}$ is a straight-chained or branched-chained $C_1$–$C_5$ alkyl group; $L^1$ is leaving group which can easily be replaced with amino, hydroxy and mercapto group; $L^2$ is leaving group which can be easily replaced with amino, and boric acid; $P^1$ is tert-butoxycarbonyl group, ethoxycarbonyl group, acetyl group, benzyloxycarbonyl group, p-methoxybenzyloxycarbonyl group, benzyl group or trifluoroacetyl group.

According to this process 1, the compound (Ia) can be obtained from the known starting compound (II).

Namely, for the first step, the compound (II) is reacted with 1.0 to 1.5 mole equivalent of ester compound (III) in the inert solvent, and if necessary in the presence of the base, under stirring at −20° C. to 150° C., preferably at 0° C. to 100° C.

The inert solvent to be used in the reaction may be benzene, toluene, tetrahydrofuran, dioxane, dimethyformamide, dimethyl sulfoxide, acetonitrile, acetone, methanol, ethanol, isopropyl alcohol, tert-butyl alcohol, ethylene glycol, diethyl ether and the like.

The base to be used in the above reaction may be an organic base such as triethylamine, diisopropylethylamine, pyridine and the like, or an inorganic base such as sodium, sodium hydride, potassium, potassium hydride, sodium methoxide, potassium tert-butoxide, sodium carbonate, potassium carbonate, cesium carbonate, cesium fluoride, sodium bicarbonate, potassium bicarbonate and the like. These organic base and inorganic base may be used in combination, and sodium iodide, potassium iodide or tetrabutylammonium iodide can be added in the reaction mixture.

The substituent "$L^1$" in the ester derivative (III) may be the leaving group which can easily be replaced with amino, hydroxy or mercapto group, and examples include halogen atom such is chlorine atom, bromine atom, iodide atom; alkylsulfonyloxy group such as methanesulfonyloxy group; arylsulfonyloxy group such as p-toluenesulfonyloxy group, 3-nitrobenzenesulfonyloxy group and the like.

The compound (II) and compound (III) to be used in this reaction can be commercially available and known compounds, or can be easily prepared from known compounds by using common methods.

Examples of the compound (II) include 4-(tert-butoxycarbonylamino)phenol, 4-(tert-butoxycarbonylamino)-2,3,5,6-tetramethylphenol, 2-(tert-butoxycarbonylamino)-3,4,5,6-tetramethylphenol, 3-(tert-butoxycarbonylamino)-2,4,5,6-tetramethylphenol, 4-(tert-butoxycarbonylamino)-2,3,5-trimethylphenol, 4-(tert-butoxycarbonylamino)-2-chloro-3,5,6-trimethylphenol, 4-(tert-butoxycarbonylamino)-2,3,6-trimethylphenol, 4-(tert-butoxycarbonylamino)-2,3,6-trimethylphenol, 4-(tert-butoxycarbonylamino)-2,3-dimethylphenol, 4-(tert-butoxycarbonylamino)-2,5-dimethylphenol, 2-(tert-butoxycarbonylamino)-4,6-dimethylphenol, 5-(tert-butoxyvarbonylamino)-2-methoxyphenol, 5-(tert-butoxycarbonylamino)-4-chloro-2-merhoxyphenol, 4-(tert-butoxycarbonylamino)-2,6-dichlorophenol, 4-(tert-utoxycarbonylamino)-2,3,4,6-tetramethylaniline, 4-methoxy-2-methylaniline, 4-(tert-butoxycarbonylamino)-2,5-dimthylaniline, 2-(tert-butoxycarbnoylamino)-4,5-dimethylaniline, 3-(tert-butoxycarbonylamino)-2,4,6-trimethylaniline, 2-(tert-butoxycarbonylamio)-4,5-dimethylaniline, 4-(tert-butoxycarbonylamino)-2,5-dichloroaniline, 4-(tert-butoxycarbonylamino)-2,6-dichloroanline, 2-(tert-butoxycarbonylamino)-4,5-dichloroaniline, 4-(tert-butoxycarbnoylamino)-2-methoxy-5-methylaniline, 4-(tert)butoxycarbonylamino)-2,5-dimethoxyaniline, 4-(enzyloxycarboylamino)phenol, 4(benzyloxycarbonylamino)-2,3,5,6-tetramethylphenol, 2-(benzyloxycarbonylamino-3,4,5,6-tetramethylphenol, 3-(benzyloxycarbonylamino)-2,4,5,6-tetramethylphenol, 4-(benzyloxycarbonylamino)-2,3,5-trimethylphenol, 4-(benzyloxycarbonylamino)-2,3,6-trimethylphenol, 4-(benzyloxycarbonylamino)-2,3-dimethylphenol, 4-(benzyloxycarbonylamino)-2,3-dimethylphenol, 2-(benzyloxycarbonylamino)-4,6-dimethylphenol, 5-(benzyloxycarbonylamino)2-methoxyphenol, 5-(benzyloxycarbonylamino)-4-chloro-2-methoxyphenol, 4-(benzyloxycarbonylamino)-2,6-dichlorophenol, 4-(benzylcarbonylamino)-2,3,4,6-tetramethylaniline, 4-methoxy-2-methylaniline, 4-(benzyloxycarbonylamino)-2,5-diethylaniline, 2-(benzyloxycarbonylamino)-4,5-dimethylaniline, 3-(benzyloxycarbonylamino)-4,5- dimethylaniline, 4-(benzyloxycarbonylamino)-2,5-dichloroaniline, 4-(benzyloxycarbonylamino)-2,6-dichloroaniline, 2-(benzyloxycarbonylamino)-4,5-dichloroaniline, 2-(benzyloxycarbonylamino)-4,5-dichloroaniline, 4-(benzyloxycarbonylamino)-2-methoxy-5-methylaniline, 4-(benzyloxycarbonylamino)-2,5-dimethoxyaniline and so on.

The ester compound of the formula (III) includes, for example, ethyl bromoacetate, ethyl 2-bromopropionate, ethyl 2-bromo-2-methylpropionate, and so on.

Then, the obtained compound (IV) is hydrogenated to convert into carboxylic acid derivative (V) by the common methods.

The compound (IX) to be used for the condensation reaction with the above-obtained carboxylic acid derivative (V) can be obtained by the following manner.

Namely, for the first step, the amine derivative (VI) is conducted by the condensation reaction with the compound (VII) in the inert solvent, and if necessary in the presence of the base, under stirring at the room temperature to 180° C., to obtain the compound (VIII).

The inert solvent to be used in the reaction may be benzene, toluene, xylene, diethylaniline, tetrahydrofuran, diethylether, dimethylformamide, dimethyl sulfoxide, dichloromethane, chloroform, methanol, ethanol, propane-2-ol, butyl alcohol and the like.

The base to be used in the above reaction may be an organic base such as triethylamine, diisopropylamine, and the like, or an inorganic base such as sodium hydride, potassium hydride, sodium tert-butoxide, potassium, tert-butoxide, sodium ethoxide, sodium carbonate, sodium bicarbonate, cesium carbonate mid the like.

The reaction of the amine compound (VI) with the compound (VII) can also be conducted in the inert solvent such as benzene, toluene, xylene and tetrahydrofuran, and in the presence of palladium catalyst such as tris(dibenzylideneacetone)dipalladium, diacetoxypalladium, palladium chloride and the like, phosphine coordination compound such as tir-n-butylphosphine, tri-tert-butylphosphine, tri-o-tolylphosphine, BINAP and the like, and the base such as sodium tert-butoxide and cesium carbonate under stirring at 50° C. to 150° C.

Furthermore, the reaction of the compound (VII), in which the substitute "$L^2$" is boronic acid residue, with the amine compound (VI) can be conducted in the inert solvent, and in the presence of the base and 1.0 to 2.0 mole equivalent of copper acetate ($CuOAc_2$), under stirring at the room temperature to 100° C. [D. M. T. Chan et al., *Tetrahedron Letters*, 39, 2933 (1998)].

The inert solvent to be used in this reaction may be dichloromethane, chloroform and the like, and the base may be triethylamine, pyridine and the like.

The compound (VI) to be used for the reaction with the compound (VII) is known compound [cf. R. H. Mach et al., *J. Med. Chem.*, 36, 3707 (1993)], or can be easily prepared by the methods described in EP 0184257 A1 [R. A. Stokbroekx, et al.].

Then the protecting group at nitrogen atom of the compound (VIII) thus obtained is removed to obtain the amine derivative (IX).

This reaction may vary depending on the protecting group on the nitrogen atom of the compound (VIII). For example, the compound (VIII) is treated with acids such as acetic acid, trifluoroacetic acid, methanesulfonic acid, trifluoromethanesulfonic acid, hydrochloric acid, sulfuric acid, or nitric acid in an inert solvent such as benzene, toluene, acetonitrile, tetrahydrofuran, dioxane, dichloromethane, chloroform, carbon tetrachloride, water, methanol, ethanol, and the like.

Furthermore, the removal of the protecting group may also be carried out by hydorgenolysis of the compound (VIII) under 1 to 5 atom of hydrogen, in the presence of a catalyst such as palladium-carbon, palladium hydroxide, platinum, or platinum oxide, in an inert solvent such as methanol, ethanol, isopropyl alcohol, ethyl acetate or acetic acid.

Then, the carboxylic acid derivative of the formula (V) is converted into amide derivative (X) by reaction with the compound (IX).

The reaction conditions of this amidation reaction may vary according to the methods described in "*Compendium for Organic Synthesis*" (wiley-Interscience: A Division of John Wiley & Sons Ltd.).

For example, the compound (V) is treated, optionally in the presence of an organic or an inorganic base, with diethyl cyanophosphonate (DEPC), diphenylphosphoryl azide (DPPA), dicyclohexylcarbodiimide (DCC), 1-ethyl-3-(dimethylamino-propyl)carbodiimide hydrochloride or 2-iodo-1-methyl-pyridiniu iodide, and then reacted with compound (IX) to obtain the amide compound (X). Furthermore, the compound (V) is converted into the activated ester compound such as acid halide. symmetric acid anhydride, or mixture acid anhydride, and then, reacted with the compound (IX),to obtain the amide compound (X).

The compound (X) thus obtained is converted into the aminophenoxyacetamide derivatives of the formula (Ia), the compound of the present invention, by the removal reaction of the protecting group on the nitrogen atom of the amide compound (X).

Although each compounds obtained in the above process 1 may be used for the next reaction without further purification, it can also be used after further purification if necessary in conventional manner such as recrystallization or column chromatography and so on.

Process 2:

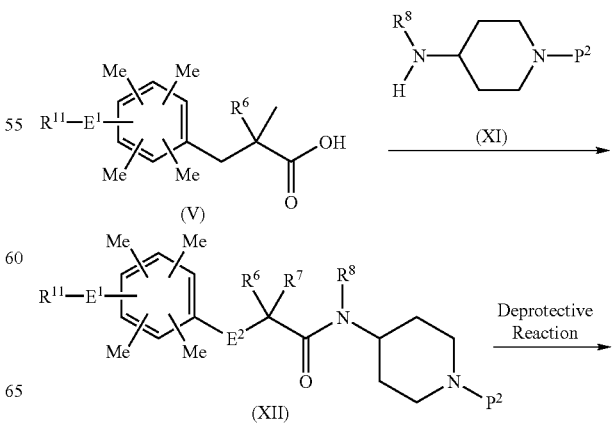

-continued

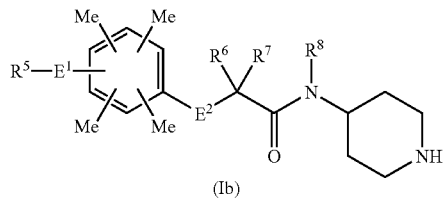

(Ib)

wherein, $R^5$ to $R^8$ and $R^{11}$ have the same definitions as above, $E^1$ and $E^2$ have the same meanings as defined in claim 2, and $p^2$ is tert-butoxycarbonyl group, ethoxycarbonyl group, acetyl group, benzyloxycarbonyl group, p-methoxybenzyloxycarbonyl group, benzyl group or trifluoroacetyl group.

According to this process 2, the aminophenoxyacetamide derivative of the formula (Ib) can be synthesized from the compound (V') [wherein $R^1$ to $R^4$ are methyl groups, $E^1$ is oxygen atom and $E^2$ is —$NR^9$; or —$NR^{10}$ and $E^1$ is oxygen atom] obtained in the process 1 mentioned above.

Namely, the compound (V') [wherein, $R^1$ to $R^4$ are methyl groups, $E^1$ is oxygen atom and $E^2$ is —$NR^9$; or $E^1$ is —$NR^{10}$ and $E^2$ is oxygen atom] is reacted with the compound (XI) to obtain the amide compound (XII), and then, the protecting group of the resultant compound (XII) is removed off to give the aminophenoxyacetamide derivative (Ib).

This reaction may be carried out by the same manner as described in the Process 1.

Process 3:

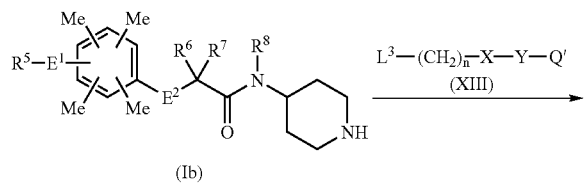

-continued

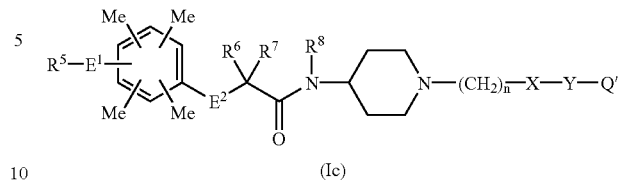

(Ic)

wherein, $R^5$ to $R^8$ and have the same definitions as above, n, X, Y, Q', $E^1$ and $E^2$ have the same meanings as defined in claim 2.

According to this process 3, the aminophenoxyacetamide derivative of the formula (Ic) can be obtained from the compound (Ib) by reacting with the compound (XIII).

Namely, the compound (Ib) is reacted with 1.0 to 1.5 mole equivalent of the compound (XIII) in the inert solvent such as benzene, toluene, tetrahydrofuran, dioxan, dimethylformamide, dimethyl sulfoxide, acetonitrile, acetone, ether, dichloromethane, chloroform and carbon tetrachloride in the presence of the base, at −50° C. to 120° C., preferably at −20° C. to 80° C.

The base to be used in the reaction may be an organic base such as triethylamine, diisopropylethylamine, pyridine and the like, or an inorganic base such as sodium, sodium hydride, potassium, potassium hydride, sodium ethoxide, sodium tert-butoxide, sodium carbonate, potassium carbonate, cesium carbonate, cesium fluoride, sodium bicarbonate, potassium bicarbonate and the like. Sodium iodide, potassium iodide or tetrabutylammonium iodide can be added in the reaction mixture.

The substituent "$L^3$" in the compound (XIII) is the leaving group, which can easily be replaced by amino group, and examples include halogen atom such as chlorine atom, bromine atom, iodine atom; alkylsulfonyloxy group such as methanesulfonyloxy group; arylsulfonyloxy group such as p-toluenesulfonyloxy group and the like.

In this process 3, the aminophenoxyacetamide derivative of the formula (Ic) can be produced as well.

Process 4:

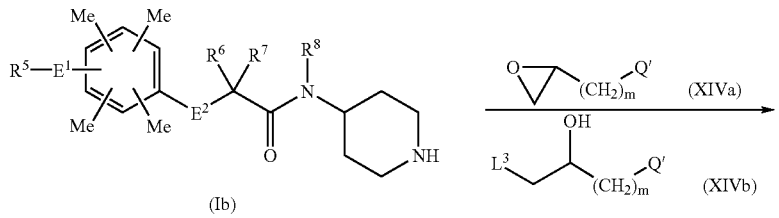

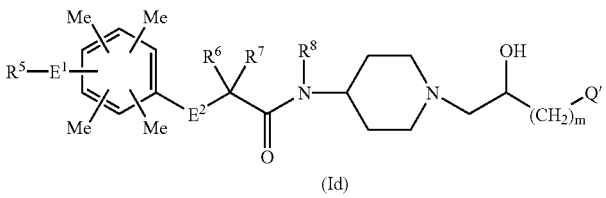

(Id)

wherein, $R^5$ to $R^8$ and $L^3$ have the same definitions as previously mentioned, $Q'$, $E^1$ and $E^2$ are the same meanings as defined in the claim 2, and m is integer 0 to 3.

According to this process 4, the aminophenoxyacetamide derivative of the formula (Id) of the present invention can be obtained from the reaction of the compound (Ib), obtained in the process 2 mentioned above, with the compound (XIVa) or the compound (XIVb).

For example, the compound (Ib) is reacted with 0.9 to 1.5 moles equivalent of the compound (XIVa) or (XIVb) in an inert solvent at from room temperature to about 200° C., preferably at about 50° C. to about 150° C., to produce the aminophenoxyacetamide of the formula (Id).

The inert solvent to be used in the reaction may be benzene, toluene, tetrahydrofuran, diethyl ether, ethylene glycol dimethyl ether, dioxane, dimethyformamide, dimethyl sulfoxide, acetonitrile, methanol, ethanol, isopropyl alcohol, tert-butyl alcohol, ethylene glycol and the like.

Examples of the compound (XIVa) include epibromohydrin, epichlorohydrin, (R)-epichlorohydrin, (S)-epichlorohydrin and the like, and examples of the compound (XIVb) include glycidyl tosylate, (R)-glycidyl tosylate, (S)-glycidyl tosylate, (R)-glycidyl 3-nitrobenzensulfonate, (S)-glycidyl 3-nitrobenzesulfonate, (R)-glycidyl 3-nitro-benzensulfonate, (S)-glycidyl 3-nitrobenzesulfonate, (R)-glycidyl 4-nitro-benzoate, (S)-glycidyl 4-nitrobenzoate, gylcidyltrimethylammonium chloride and the like.

In this process 4, the aminophenoxyacetamide derivative of the formula (Id) can be produced as well.

The aminophenoxyacetamide derivatives of the formula (I) thus obtained may be isolated and purified in conventional manner, such as recrystallization, column chromatography and the like.

Further, each isomers contained in the compounds of the formula (I) of the present invention can be obtained by resolution of the isomeric mixture of these compounds by the conventional methods, such as recrystallization, column chromatography, HPLC, aria the like, or by using optically active reagents.

The aminophenoxyacetamide derivatives of the present invention represented by the formula (I) may be used in the form of free bases or suitable pharmaceutically acceptable acid addition salts thereof. The pharmaceutically acceptable salts can be obtained by treating the compound (I) with an inorganic acid or an organic acid in suitable organic solvent such as ether, tetrahydrofuran, dichloromethane, chloroform, benzene, toluene, methanol, isopropanol, ethanol and the like.

Examples of the inorganic acid include hydrochloric acid, sulfuric acid, hydrobromic acid, phosphoric acid, periodic acid and the like. Further, examples of the organic acid include formic acid, acetic acid, butyric acid, oxalic acid, malonic acid, propionic acid, valeric acid, succinic acid, fumaric acid, maleic acid, tartaric acid, citric acid, malic acid, benzoic acid, p-toluenesulfonic acid, methanesulfonic acid and the like.

The aminophenoxyacetamide derivatives of the present invention represented by the formula (I) or pharmaceutically acceptable salts thereof shows low toxicity and may be administered per se. However, it may be converted in the form of pharmaceutically acceptable composition with the conventional pharmaceutically acceptable carriers for improvement or treatment of various kinds of diseases due to cerebral functional or organic disorder.

The dosage forms may include oral formulations such as capsules, tablets or parenteral formulations such as injection solution containing the compound of the formula (I) per se, or using the conventional excipients. For example, the capsules can be prepared by mixing the compound of the formula (I) in powder form with a suitable excipient such as lactose, starch or derivatives thereof or cellulose derivatives, and then filled in gelatin capsules.

Also, the tablets can be prepared by mixing the active ingredients with the above-mentioned excipients, binders such as sodium carboxymethylcellulose, alginic acid or gum arabic and water, then if necessary, making the resultant mixture into granules. Then, it may be further mixed with lubricant such as talc or stearic acid, and compressed into tablet by mean of common tableting machine.

Injectable formulations for parenteral route also can be prepared by dissolving the compound of the formula (I) or salts thereof in sterile distilled solution or sterile physiological saline solution with solution adjuvant, and filling it into ample. A stabilizer or buffer can be used in the injectable solution, and the injectable formulation may be administered intravenously or by dripping.

In administration of the compound of the formula (I), which possesses neuroprotective effect by induction of CalbindinD-28k, one of $Ca^{2+}$-bindind proteins, the therapeutically effective dosage for improving cerebral functional and organic disorders is not particularly limited and may vary depending on the various kinds of factors. These factors may be the patient's condition, the severity of the disease, age, existence of a complication, administration route, formulation, as well as number of times for administration.

A usual recommended daily dose for oral administration is within the range of 0.1–1,000 mg/day/person, preferably 1–500 mg/day/person, while a usual recommended daily dose for parenteral administration is within the range of $\frac{1}{100}$ to $\frac{1}{2}$ based on dose of the oral administration. These doses also may vary depending on age, as well as the patient's condition.

EXAMPLES

The present invention is illustrated in more detail by way of the following examples, but it is to be noted that the present invention is not limited by these Examples in any way.

The compound numbers in the following examples are identical to those of the Table's mentioned later.

Example 1

2-(4-Amino-2,3,5,6-tetramethylphenoxy)-N-methyl-N-(4-piperidinyl)acetamide (1)

A solution of 457 mg of 2-[4-(tert-butoxycarbonylamino)-2,3,5,6-tetramethylphenoxy]acetic acid, 363 mg of 1-(tert-butoxycarbonylamino)-4-methylamiopiperidine, 2.16 g og 25% propane phosphonic acid anhydride [Japanese Patent Kokai Showa 55-100346] in ethyl acetate solution and 985 µl of triethylamine in 5 ml of dichloromethane was stirred over night under room temperature. After the reaction, saturated sodium hydrogen carbonate aqueous solution was added to the reaction mixture and the mixture was extracted with dichloromethane. The extract was washed with saline, dried and concentrated under reduced pressure to give the residue. The obtained residue was dissolved in 8 ml of dichloromethane, and to this solution was added 2 ml of trifluoroacetic acid under ice-cooling, then the mixture was stirred for 1 hour at the room temperature. After removal of the solvent, the resultant residue was purified by amine-coated silica gel (Fuji Silysia Chemical Ltd.) column chromatography (dichloromethane : methanol =30:1) to give 192 mg (42%) of the above-mentioned compound (1).

Example 2

2-(4-Amino-2,3,5,6-tetramethylphenoxy)-N-methyl-(4-piperidinyl)propanamide (2)

The title compound (2) was obtained from 2-[4-(tert-butoxycarbonylamino)-2,3,5,6-tetramethylphenoxy]propionic acid and 1-(tert-butoxycarbonylamino)-4-methylaminopiperidine by the same manner as the Example 1.

Example 3

2-(4-Amino-2,3,5,6-tetramethylphenoxy)-2-methyl-N-methyl-N-(4-piperidinyl)propanamide (3)

The title compound (3) was obtained from 2-[4-(tert-butoxycarbonylamino)-2,3,5,6-tetramethylphenoxy]-2-methyl propionic acid and 1-(tert-butoxycarbonylamino)-4-methylaminopiperidine by the same manner as the Example 1.

Example 4

2-(2-Amino-3,4,5,6-tetramethylphenoxy)-N-methyl-N-(4-piperidinyl)acetamide (4)

The title compound (4) was obtained from 2-[2-(tert-butoxycarbonylamino)-3,4,5,6-tetramethylphenoxy]acetic acid and 1-(tert-butoxylcarbonylamino)-4-methylaminopiperidine by the same manner as the Example 1.

Example 5

2-(3-Amino-2,4,5,6-tetramethylphenoxy)-N-methyl-N-(4-piperidinyl)acetamide (5)

The title compound (5) was obtained from 2-[3-(tert-butoxycarbonylamino)-2,4,5,6-tetramethylphenoxy]acetic acid and 1-(tert-butoxycarbonylamino)-4-methylaminopiperidine by the same manner as the Example 1.

Example 6

2-(4-Amino-2,3,5,6-tetramethylphenoxy)-N-methyl-N-(1-phenethyl-4-piperidinyl)acetamide (6)

To a mixture solution of 99 mg of the compound (1) obtained in the Example 1 and 42.3 μl of phenethyl bromide in 2 ml of acetonitrile was added 65 μl of triethylamine, and the mixture was stirred for 5 hours at 60° C. After the reaction, saturated sodium hydrogen carbonate aqueous solution was added to the reaction mixture and the mixture was extracted with ethyl acetate. The extract was washed with saline, dried and concentrated under reduced pressure to give the residue. The obtained residue was purified by amine-coated silica gel (Fuji Silysia Chemical Ltd.) column chromatography (dichloromethane : ether =1:1) to give 86 mg (65%) of the above-mentioned compound (6).

Example 7

2-(4-Amino-2,3,5,6-tetramethylphenoxy)-N-[1-(2-anilino-2-oxoethyl)-4-piperidinyl]-N-methylacetamide (7)

The title compound (7) was obtained from the compound (1) obtained in the Example 1 and N-phenyl-2-bromoacetamide by the same manner as the Example 6.

Example 8

2-(4-Amino-2,3,5,6-tetramethylphenoxy)-N-(1-benzoyl-4-piperidinyl)-N-methylacetamide (8)

The title compound (8) was obtained from the compound (1) obtained in the Example 1 and benzoyl chloride by the same manner as the Example 6.

Example 9

2-(4-Amino-2,3,5,6-tetramethylphenoxy)-N-(1-butyl-4-piperidinyl)-N-methylacetamide (9)

The title compound (9) was obtained from the compound (1) obtained in the Example 1 and butyl bromide by the same manner as the Example 6.

Example 10

2-(4-Amino-2,3,5,6-tetramethylphenoxy)-N-[1-(2-phenyl-2-oxoethyl)-4-piperidinyl]-N-methylacetamide (10)

The title compound (10) was obtained from the compound (1) obtained in the Example 1 and phenacyl bromide by the same manner as the Example 6.

Example 11

2-(4-Amino-2,3,5,6-tetramethylphenoxy)-N-[1-(2-hydroxy-2-phenylethyl)-4-piperidinyl]-N-methylacetamide (11)

To a mixture solution of the compound (10) obtained in the Example 10 in methanol was added 1.0 equivalent of sodium borohydride at 0° C., and the mixture was stirred for 1.5 hours at the room temperature. After the reaction, the solvent was removed under reduced pressure, and the resulting residue was purified by amine-coated silica gel (Fuji Silysia Chemical Ltd.) column chromatography (dichloromethane : methanol =20:1) to give the above-mentioned compound (11) in the yield of 58%.

Example 12

2-(4-Amino-2,3,5,6-tetramethylphenoxy)-N-(1-cyclo-propylmethyl-4-piperidinyl)-N-methylacetamide (12)

The title compound (12) was obtained from the compound (1) obtained in the Example 1 and cyclopropylmethyl bromide by the same manner as the Example 6.

Example 13

2-(4-Amino-2,3,5,6-tetramethylphenoxy)-N-methyl-N-[1-(trans-2-phenyl-1-cyclopropylmethyl)-4-piperidinyl]acetamide (13)

The title compound (13) was obtained from the compound (1) obtained in the Example 1 and trans-2-phenyl-1-cyclopropylmethyl bromide by the same manner as the Example 6.

Example 14

2-(4-Amino-2,3,5,6-tetramethylphenoxy)-N-methyl-N-[1-(2-phenoxyethyl)-4-piperidinyl]acetamide (14)

The title compound (14) was obtained from the compound (1) obtained in the Example 1 and 2-phenoxyethyl bromide by the same manner as the Example 6.

Example 15

2-(4-Amino-2,3,5,6-tetramethylphenoxy)-N-methyl-N-{1-[2-(N-methylanilino)-2-oxoethyl]-4-piperidinyl}acetamide (15)

The title compound (15) was obtained from the compound (1) obtained in the Example 1 and N-methyl-N-phentyl-2-bromoacetamide by the same manner as the Example 6.

Example 16

2-(4-Amino-2,3,5,6-tetramethylphenoxy)-N-methyl-N-{1-[2-(4-morpholinyl)ethyl]-4-piperidinyl}acetamide (16)

The title compound (16) was obtained from the compound (1) obtained in the Example 1 and N-(2-bromoethyl)morpholine hydrochloride by the same manner as the Example 6.

Example 17

2-(4-Amino-2,3,5,6-tetramethylphenoxy)-N-{1-[2-(2-hydroxy-2-phenylethoxy)ethyl]-4-piperidinyl}-N-methylacetamide (17)

The title compound (17) was obtained from the compound (1) obtained in the Example 1 and 2-(chloroethoxy)-1-phenylethanol by the same manner as the Example 6.

Example 18

2-(4-Amino-2,3,5,6-tetramethylphenoxy)-N-[1-(4-cyano-benzyl)-4-piperidinyl]-N-methylacetamide (18)

The title compound (18) was obtained from the compound (1) obtained in the Example 1 and 4-cyanobenzyl bromide by the same manner as the Example 6.

Example 19

4-({4-[[(4-Amino-2,3,5,6-tetramethylphenoxy)acetyl]-(methyl)amino]-1-piperidinyl}methyl)bezamide (19)

To a mixture solution of 82 mg of the compound (18) obtained in the Example 18 in methanol were added 58 μl of 30% hydrogen peroxide aqueous solution and 150 μl of 3N-sodium hydroxide aqueous solution under ice-cooling, and the reaction mixture was stirred for 6 hours at the room the temperature. After the reaction, saturated sodium hydrogen carbonate aqueous solution was added to the reaction mixture, and extracted with dichloromethane. The organic layer was washed with saturated saline, dried and the solvent was removed under reduced pressure. The resulting residue was purified by amine coated silica gel (Fuji Silysia Chemical Ltd.) column chromatography (dichloromethane : methanol =10:1) to give 66 mg (77%) of the above-mentioned compound (19).

Example 20

2-(4-Amino-2,3,5,6-tetramethylphenoxy)-N-methyl-N-{1-[2-(phenylthio)ethyl]-4-piperidinyl}acetamide (20)

The title compound (20) was obtained from the compound (1) obtained in the Example 1 and 2-(chloroethyl)phenyl sulfide by the same manner as the Example 6.

Example 21

2-(4-Amino-2,3,5,6-tetramethylphenoxy)-N-methyl-N-[1-(2-propynyl)-4-piperidinyl]acetamide (21)

The title compound (21) was obtained from the compound (1) obtained in the Example 1 and propargyl bromide by the same manner as the Example 6.

Example 22

2-(4-Amino-2,3,5,6-tetramethylphenoxy)-N-methyl-N-[1-(1-methyl-2-phenylethyl)-4-piperidinyl]acetamide (21)

The title compound (22) was obtained from the compound (1) obtained in the Example 1 and 2-bromo-1-phenylpropane by the same manner as the Example 6.

Example 23

2-(4-Amino-2,3,5,6-tetramethylphenoxy)-N-(1-cyclo-propylmethyl-4-piperidinyl)-N-methylpropanamide (23)

The title compound (23) was obtained from the compound (2) obtained in the Example 2 and cyclopropylmethyl bromide by the same manner as the Example 6.

Example 24

2-(4-Amino-2,3,5,6-tetramethylphenoxy)-N-(1-butyl-4-piperidinyl)-N-methylpropanamide (24)

The title compound (24) was obtained from the compound (2) obtained in the Example 2 and 1-bromobutane by the same manner as the Example 6.

Example 25

2-(4-Amino-2,3,5,6-tetramethylphenoxy)-N-methy-N-{1-[2-(4-morpholinyl)ethyl]-4-piperidinyl}proanamide (25)

The title compound (25) was obtained from the compound (2) obtained in the Example 2 and N-(2-bromoethyl)morpholine hydrochloride by the same manner as the Example 6.

Example 26

2-(4-Amino-2,3,5,6-tetramethylphenoxy)-N-methyl-N-[1-(trans-2-phenyl-1-cyclopropylmethyl)-4-piperidniyl]propanamide (26)

The title compound (26) was obtained from the compound (2) obtained in the Example 2 and trans-2-phenyl-1-cyclopropylmethyl bromide by the same manner as the Example 6.

Example 27

2-(4-Amino-2,3,5,6-tetramethylphenoxy)-N-methyl-N-{1-[2-(N-methylanilino)-2-oxoethyl]-4-piperidinyl}propanamide (27)

The title compound (27) was obtained from the compound (2) obtained in the Example 2 and N-methyl-N-phenyl-2-bromoacetamide by the same manner as the Example 6.

Example 28

2-(4-Amino-2,3,5,6-tetramethylphenoxy)-N,2-dimethyl-N-[1-(2-phenylethyl)-4-piperidinyl]propanamide (28)

The title compound (28) was obtained from the compound (3) obtained in the Example 3 and phenethyl bromide by the same manner as the Example 6.

Example 29

2-(2-Amino-3,4,5,6-tetramethylphenoxy)-N-methyl-N-[1-(2-phenylethyl)-4-piperidinyl]acetamide (29)

The title compound (29) was obtained from the compound (4) obtained in the Example 4 and phenethyl bromide by the same manner as the Example 6.

Example 30

2-(2-Amino-3,4,5,6-tetramethylphenoxy)-N-[1-(2-phenyl-2-oxoethyl)-4-piperidinyl]-N-methylacetamide (30)

The title compound (30) was obtained from the compound (4) obtained in the Example 4 and phenacyl bromide by the same manner as the Example 6.

Example 31

2-(2-Amino-3,4,5,6-tetramethylanilino)-N-methyl-N-[1-(4-phenoxyphenyl)-4-piperidinyl] acetamide (31)

The title compound (31) was obtained from 2-[2-(tert-butoxycarbonylamino)-3,4,5,6-tetramethylanilino]acetic acid 1-(4-phenoxyphenyl)-4-methyaminopiperidine by the same manner as the Example 1.

Example 32

2-(2-Amino-3,4,5,6-tetramethylanilino)-N-{1-[4-(4-fluorobenzyl)phenyl]-4-piperidinyl}-N-methylacteamide (32)

The title compound (32) was obtained from 2-[2-(tert-butoxycarbonylamino)-3,4,5,6-tetramethylanilino]acetic acid 1-[4-(4-fluorobenzyl)phenyl]-4-methyaminopiperidine by the same manner as the Example 1.

Example 33

2-(3-Amino-2,4,5,6-tetramethylphenoxy)N-(1-benzoyl-4-piperidinyl)-N-methylacetamide (33)

The title compound (33) was obtained from the compound (5) obtained in the Example 5 and benzoyl chloride by the same manner as the Example 6.

Example 34

2-(3-Amino-2,4,5,6-tetramethylphenoxy)-N-[1-(4-cyano-benzyl)-4-piperidinyl]-N-methylacetamide (34)

The title compound (34) was obtained from the compound (5) obtained in the Example 5 and 4-cyanobenzyl bromide by the same manner as the Example 6.

Example 35

2-(3-Amino-2,4,5,6-tetramethylphenoxy)-N-methy-N-[1-(2-phenylethyl)-4-piperidinyl ] acetamide (35)

The title compound (35) was obtained from the compound (5) obtained in the Example 5 and phenethyl bromide by the same manner as the Example 6.

Example 36

2-(4-Amino-2,3,5-trimethylphenoxy)-N-[1-(4-fluoro-phenyl)-4-piperidinyl]-N-methylacetamide (36)

The title compound (36) was obtained from 2-[4-(tert-butoxycarbonylamino)-2,3,5-trimethylphenoxy]acetic acid and Example 1.

Example 37

2-(4-Amino-2,3,5,6-tetramethylanilino)-N-[1-(1,3-benzothiazol-2-yl)-4-piperidinyl]-N-methylacetamide (37)

The title compound (37) was obtained from 2-[4-(tert-butoxycarbonylamino)-2,3,5,6-tetramethylanilino]acetic acid and 1-(1,3-benzothiazol-2-yl)-4-methyaminopiperidine by the same, manner as the Example 1.

Example 38

2-(4-Amino-2,3,5,6-tetramethylanilino)-N-[1-(4-fluorophenyl)-4-piperidinyl]-N-methylacetamide (38)

The title compound (38) was obtained from 2-[4-(tert-butoxycarbonylamino)-2,3,5,6-tetramethylanilino]acetic acid 1-(4-fluorophenyl)-4-methyaminopiperidine by the same manner as the Example 1.

Example 39

2-(3-Amino-2,4,6-trimethylanilino)-N-[1-(4-fluorophenyl)-4-piperidinyl]-N-methylacetamide (39)

The title compound (39) was obtained from 2-[3-(tert-butoxycarbonylamino)-2,4,6-trimethylanilino]acetic acid and Example 1.

Example 40

2-(4-Amino-2,3,5,6-tetramethylanilino)-N-methyl-N-[1-(4-phenoxyphenyl)-4-piperidinyl]propanamide (40) (40)

The title compound (40) was obtained from 2-[4-(tert-butoxycarbonylamino)-2,3,5,6-tetramethylanilino]propionic acid and 1-(4-phenoxyphenyl)-4-methyaminopiperidine by the same manner as the Example 1.

Example 41

2-(4-Amino-2,3,5,6-tetramethylanilino)-N-(1-[1,1'-biphenyl]-4-yl-4-piperidinyl)-N-methylpropanamide (41)

The title compound (41) was obtained from 2-[4-(tert-butoxycarbonylamino)-2,3,5,6-tetramethylanilino]propionic acid and 1-[1,1'-biphenyl]-4-yl-N-methyl-4-piperidine amine by the same manner as the Example 1.

The physiochemical datum of the compounds obtained by the above-mentioned examples is summarized in the following tables 1 to 7.

TABLE 1

| No. | Chemical Structure | Properties | IR (KBr) cm⁻¹ | ¹H-NMR (CDCl₃) |
|---|---|---|---|---|
| 1 | (structure: 4-amino-2,3,5,6-tetramethylphenoxy-CH₂-C(O)-N(CH₃)-(4-piperidinyl)) | white powder | (CHCl₃) 2950, 2399, 1734, 1652, 1558, 1472, 1418, 1319, 1083 | 1.53–1.85(4H, m), 2.08(3H, s), 2.09(3H, s), 2.23(3H, s), 2.24(3H, s), 2.63(1H, m), 2.76(1H, m), 2.88&2.92(3H, each s), 3.15(2H, m), 3.48(2H, brs), 3.73&4.63(1H, each m), 4.31&4.36(2H, each s) |
| 2 | (structure: 4-amino-2,3,5,6-tetramethylphenoxy-CH(CH₃)-C(O)-N(CH₃)-(4-piperidinyl)) | white powder | 3378, 2938, 1638 1472, 1416, 1370 1286, 1257, 1077 | 1.42&1.43(3H, d, J=6.5Hz), 1.54–1.72(4H, m), 2.08(6H, s), 2.19(6H, s), 2.35&2.53(1H, each m), 2.74(1H, m), 2.80&2.84 (3H, each s), 3.08(2H, m), 3.44(2H, brs), 3.80(0.5H, m), 4.58 (1.5H, m) |
| 3 | (structure: 4-amino-2,3,5,6-tetramethylphenoxy-C(CH₃)₂-C(O)-N(CH₃)-(4-piperidinyl)) | pale yellow powder | (CHCl₃) 2401, 1624, 1474 1412, 1384, 1256 1145, 1076 | 1.41(6H, s), 1.61–1.80(4H, m), 2.04&2.07&2.08&2.11&2.13 (12H, each s), 2.65(1H, s), 2.75(1H, m), 2.89&3.34(3H, each s), 3.14(2H, m), 3.45(2H, brs), 4.60&4.90(1H, m) |

TABLE 1-continued

| No. | Chemical Structure | Properties | IR (KBr) cm⁻¹ | ¹H-NMR (CDCl₃) |
|---|---|---|---|---|
| 4 | 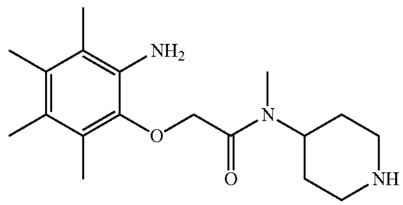 | white powder | (CHCl₃) 2401, 1654, 1474, 1238, 1077, 1044, 928 | 1.49–1.73(4H, m), 2.10(3H, s), 2.13(3H, s), 2.17(3H, s), 2.22 (3H, s), 2.53–2.81(2H, m), 2.76&2.91(3H, each s), 3.14(2H, m), 3.40&4.61(1H, m), 3.96–4.33(2H, brs), 4.47&4.51(2H, each s) |
| 5 | 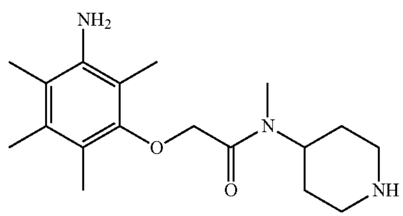 | yellow oil | (CHCl₃) 2932, 2402, 1654, 1451, 1320, 1122, 1084, 1050 | 1.61–1.81(4H, m), 2.09&2.13&2.18&2.22(12H, each s), 2.63 (2H, m), 2.77(2H, m), 2.88&2.92(3H, each s), 3.16&3.18(2H, each m), 3.52(2H, brs), 3.72&4.63(1H, each m), 4.34&4.38 (2H, each s) |

TABLE 2

| No. | Chemical Structure | Properties | IR (KBr) cm⁻¹ | ¹H-NMR (CDCl₃) |
|---|---|---|---|---|
| 6 | (structure) | white powder (2.HCl salt) (Et₂O/MeOH) 261–263° C. | (2.HCl salt) 3432, 2926, 2345, 1646, 1534, 1478, 1455, 1304, 1248, 1098 | 1.56–2.29(6H, m), 2.09(6H, s), 2.23(3H, s), 2.24(3H, s), 2.61(2H, m) 2.75–2.85(2H, m), 2.88&2.92(3H, each s), 3.09(2H, m), 3.47(2H, brs) 3.69&4.58(1H, each m), 4.32&4.35(2H, each s), 7.20(3H, m), 7.24–7.33(2H, m) |
| 7 | (structure) | white powder (2.HCl salt) (Et₂O/MeOH) 196–200° C. | (2.HCl salt) 3425, 2950, 1692, 1636, 1556, 1498, 1447, 1314, 1248, 1097 | 1.68–2.04(4H, m), 2.09(6H, s), 2.23(6H, s), 2.29–2.55(2H, m), 2.94&2.96(3H, each s), 3.00(2H, m), 3.14&3.16(2H, each s), 3.49(2H, brs), 3.81&4.57(1H, each m), 4.33&4.36(2H, each s), 7.12(1H, m), 7.35(2H, m), 7.57(2H, d), 8.96&9.06(1H, each brs) |
| 8 | (structure) | white powder (HCl salt) (Et₂O/MeOH) 202–203° C. | (2.HCl slat) 3457, 2922, 2586 1633, 1530, 1448, 1318, 1250, 1108 1043, 713 | 1.78(4H, m), 2.08(6H, s), 2.22(6H, s), 2.89(3H, s), 2.89–3.06 (2H, brs), 3.47(2H, brs), 3.87(1H, brs), 4.06&4.79(1H, each m), 4.32&4.37(2H, each s), 4.82(1H, brs), 7.41(5H, m) |
| 9 | (structure) | white powder (2.HCl salt) (Et₂O/MeOH) 229–230° C. | (2.HCl salt) 3428, 2956, 1648, 1522, 1463, 1419, 1309, 1248, 1106, 1091, 1046 | 0.92(3H, m), 1.33&1.45(4H, each m), 1.74–2.32(8H, m), 2.08 (6H, s), 2.22(6H, s), 2.88&2.90(3H, each s), 2.99&3.01(2H, each m), 3.46 (2H, brs), 3.68&4.11&4.54(1H, each m), 4.31& 4.34(2H, each s). |

TABLE 2-continued

| No. | Chemical Structure | Properties | IR (KBr) cm⁻¹ | ¹H-NMR (CDCl₃) |
|---|---|---|---|---|
| 10 | (structure) | white powder (2.HCl salt) (Et₂O/MeOH) 201–203° C. | (2.HCl salt) 3417, 2938, 1694, 1646, 1598, 1450, 1417, 1247, 1101 | 1.69(2H, m), 1.89(1H, m), 2.08(6H, s), 2.22(6H, s), 2.30(1H, m), 2.89(3H, s), 2.91&3.09(4H, each m), 3.74&4.59&4.81(1H, each s), 3.82&3.85(2H, each s), 4.32&4.35(2H, each s), 7.46& 7.57(3H, each m), 7.97(2H, m) |
| 11 | (structure) | white powder (2.HCl salt) (Et₂O/MeOH) 229–230° C. | (2.HCl salt) 3375, 2945, 1646, 1460, 1248, 1100, 700 | 1.73–2.56(8H, m), 2.09(6H, s), 2.23(6H, s), 2.90&3.25(2H, each m), 2.90&2.92(3H, each s), 3.47(2H, brs), 3.76&4.58(1H, each m), 4.33&4.35(2H, each s), 4.71&4.73(1H, each m), 7.36(5H, m) |

TABLE 3

| No. | Chemical Structure | Properties | IR (KBr) cm$^{-1}$ | $^1$H-NMR (CDCl$_3$) |
|---|---|---|---|---|
| 12 | 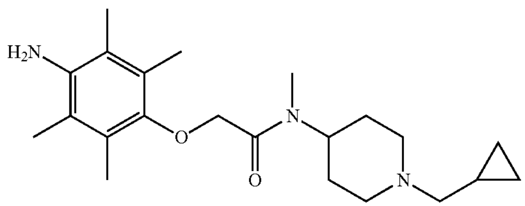 | white powder (2.HCl salt) (Et$_2$O/MeOH) 223–225° C. | (2.HCl salt) 3425, 2932, 1648, 1460, 1414, 1306, 1248, 1095, 1032 | 0.11(2H, m), 0.41(2H, m), 0.75&0.95(1H, each m), 1.65–2.18 (8H, m), 1.99(6H, s), 2.10&2.13(6H, each s), 2.78&2.81(3H, each s), 3.05(2H, m), 3.37(2H, brs), 3.58&4.44(1H, each m), 4.21&4.24&4.27(2H, each s) |
| 13 | 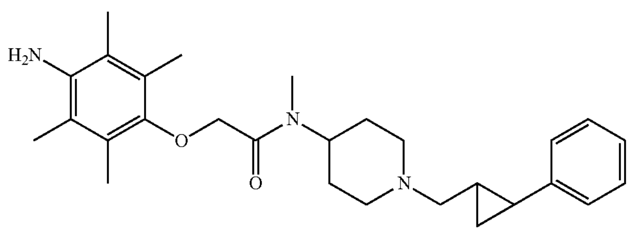 | white powder (2.HCl salt) (Et$_2$O/MeOH) 216–217° C. | (2.HCl salt) 3431, 2941, 1637, 1498, 1460, 1417, 1248, 1096, 1032 | 0.82(1H, m), 0.97(1H, m), 1.23(1H, m), 1.66–2.22(7H, m), 2.08 (6H, s), 2.22(6H, s), 2.37(1H, m), 2.53(1H, m), 2.87&2.90(3H, each s), 3.12(2H, m), 3.46(2H, brs), 3.67&4.54(1H, each m), 4.31&4.33(2H, each s), 7.04(2H, m), 7.14(1H, m), 7.25(2H, m) |
| 14 | 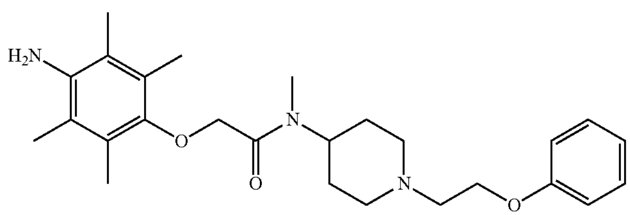 | white powder (2.HCl salt) (Et$_2$O/MeOH) 216–219° C. | (2.HCl salt) 3417, 2950, 1638, 1599, 1494, 1413, 1305, 1246, 1099, 1044, 756 | 1.61–2.38(6H, m), 2.09(6H, s), 2.22(6H, s), 2.82(2H, m), 2.88& 2.91(3H, each s), 3.08(2H, m), 3.46(2H, brs), 3.70&4.56(1H, each m), 4.09(2H, m), 4.31&4.34(2H, each s), 6.90(3H, m), 7.28(2H, m) |
| 15 | 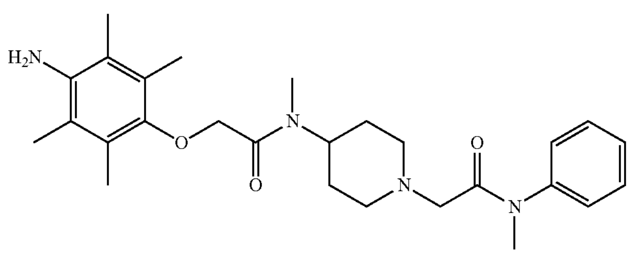 | white powder (2.HCl salt) (Et$_2$O/MeOH) 210–212° C. | (2.HCl salt) 3414, 2938, 1663, 1495, 1452, 1388, 1248, 1098, 703 | 1.79–2.20(6H, m), 2.07(6H, s), 2.17&2.21(6H, each s), 2.84& 2.88(3H, each s), 2.92(4H, m), 3.27(3H, s), 3.47(2H, m), 3.57& 4.47(1H, m), 4.29&4.30(2H, each s), 7.18(2H, d=7.3Hz), 7.36–7.45(3H, m) |

TABLE 3-continued

| No. | Chemical Structure | Properties | IR (KBr) cm$^{-1}$ | $^1$H-NMR (CDCl$_3$) |
|---|---|---|---|---|
| 16 | (structure: H$_2$N-trimethylphenyl-O-CH$_2$-C(=O)-N(CH$_3$)-piperidine-N-CH$_2$CH$_2$-morpholine) | white powder (3.HCl salt) (Et$_2$O/MeOH) 290–293° C. | (3.HCl salt) 3442, 2945, 2402, 1668, 1452, 1306, 1294, 1248, 1121, 1102, 1060, 876 | 1.75–2.23(6H, m), 2.09(6H, s), 2.22(6H, s), 2.50(8H, m), 2.87&2.90(3H, each s), 3.01(2H, m), 3.47(2H, m), 3.47&4.54(1H, each m), 3.71(4H, m), 4.30&4.34(2H, each s) |
| 17 | (structure: H$_2$N-trimethylphenyl-O-CH$_2$-C(=O)-N(CH$_3$)-piperidine-N-CH$_2$CH$_2$-O-CH$_2$-CH(OH)-phenyl) | white powder (2.HCl salt) (Et$_2$O/MeOH) 228–231° C. | (2.HCl salt) 3427, 2950, 1651, 1452, 1415, 1306, 1248, 1124, 1101, 1045, 700 | 1.67–2.24(6H, m), 2.09(6H, s), 2.22&2.23(6H, each s), 2.61 (2H, m), 2.79(2H, m), 2.89&2.92(3H, each m), 3.08(2H, m), 3.43 (2H, m), 3.47(2H, brs), 3.70&4.57(1H, each m), 3.75(2H, m), 4.32&4.35(2H, each s), 4.87(1H, m), 7.23(5H, m) |

TABLE 4

| No. | Chemical Structure | Properties | IR (KBr) cm⁻¹ | ¹H-NMR (CDCl₃) |
|---|---|---|---|---|
| 18 | (structure: H₂N-trimethylphenyl-O-CH₂-C(=O)-N(CH₃)-piperidine-N-CH₂-C₆H₄-CN) | white powder (2.HCl salt) (Et₂O/MeOH) 251–253° C. | (2.HCl salt) 3416, 2918, 2487, 1658, 1631, 1461, 1305, 1248, 1116, 1097 | 1.66–2.22(6H, m), 2.08(6H, s), 2.22(6H, s), 2.89&2.92(3H, each s), 2.91(2H, m), 3.47(2H, brs), 3.55(2H, s), 3.70&4.55(1H, each m), 4.31&4.34(2H, each s), 7.44(2H, m), 7.60(2H, m) |
| 19 | (structure: H₂N-trimethylphenyl-O-CH₂-C(=O)-N(CH₃)-piperidine-N-CH₂-C₆H₄-CONH₂) | white powder (2.HCl salt) (Et₂O/MeOH) 226–229° C. | (2.HCl salt) 3404, 2940, 1667, 1462, 1421, 1248, 1247, 1096, 1026, 1097 | 1.65–2.22 (6H, m), 2.08(6H, s), 2.21(6H, s), 2.88&2.91(3H, each s), 2.93(2H, m), 3.46(2H, brs), 3.53(2H, s), 3.66&4.54(1H, each m), 4.31&4.33(2H, each s), 4.39(2H, m), 4.77(2H, m), 5.74&6.12(2H, brs) |
| 20 | (structure: H₂N-trimethylphenyl-O-CH₂-C(=O)-N(CH₃)-piperidine-N-CH₂CH₂-S-C₆H₅) | white powder (2.HCl salt) (Et₂O/MeOH) 231–233° C. | (2.HCl salt) 3427, 2936, 1640, 1459, 1419, 1308, 1247, 1096, 1026, 746, 693 | 1.67–2.22(6H, m), 2.08(6H, s), 2.22(6H, s), 2.63(2H, m), 2.87&2.90(3H, each s), 3.03–3.07(4H, m), 3.67&4.53(1H, each m), 4.11&4.13(2H, each s), 7.18(1H, m), 7.27(2H, m), 7.34(2H, m) |
| 21 | (structure: H₂N-trimethylphenyl-O-CH₂-C(=O)-N(CH₃)-piperidine-N-CH₂-C≡CH) | white powder (2.HCl salt) (Et₂O/MeOH) 172–174° C. | (2.HCl salt) 3406, 2926, 2565, 1638, 1459, 1420, 1249, 1099 | 1.65–2.43(7H, m), 2.09&2.22&2.24&2.26 (12H, each s), 2.88&2.91(3H, each s), 2.97(2H, m), 3.31(2H, s), 3.47(2H, brs), 3.68&4.56(1H, each m), 4.31&4.35(2H, each s) |

TABLE 4-continued

| No. | Chemical Structure | Properties | IR (KBr) cm⁻¹ | ¹H-NMR (CDCl₃) |
|---|---|---|---|---|
| 22 | (2,3,5-trimethyl-4-aminophenoxy)acetamide with N-methyl, 1-(1-phenylpropan-2-yl)piperidin-4-yl | white powder (2.HCl salt) (Et₂O/MeOH) 212–214° C. | (2.HCl salt) 3411, 2936, 1638, 1454, 1420, 1249, 1098, 1028 | 0.94(3H, t), 1.46–2.26(4H m), 2.09&2.23&2.24(12H, each s), 2.30–2.55(2H, m), 2.80–3.03(4H, m), 2.89&2.92(3H, each s), 3.47(3H, m), 3.63&4.54(1H, m), 4.32&4.35(2H, each s), 7.13–7.33 (5H, m) |
| 23 | (2,3,5-trimethyl-4-aminophenoxy)propanamide with N-methyl, 1-(cyclopropylmethyl)piperidin-4-yl | white powder (2.HCl salt) (Et₂O/MeOH) 220–221° C. | (2.HCl salt) 3408, 2939, 2592, 1657, 1463, 1415, 1251, 1107, 1079, 1024 | 0.01&0.43(4H, each m), 0.76(1H, m), 1.34&1.35(3H, d, J=6.2 Hz), 1.50–1.83(6H, m), 1.99(6H, s), 2.06–2.23(2H, m), 2.11(6H, s), 2.72&2.76(3H, each s), 3.02(2H, m), 3.36(2H, brs), 3.60& 4.43(1H, each m), 4.47(1H, m) |

TABLE 5

| No. | Chemical Structure | Properties | IR (KBr) cm$^{-1}$ | $^1$H-NMR (CDCl$_3$) |
|---|---|---|---|---|
| 24 | (structure: 4-amino-2,3,5,6-tetramethylphenoxy propanamide linked to N-methyl-4-(1-butylpiperidinyl)) | white powder (2.HCl salt) (Et$_2$O/MeOH) 228–231° C. | (2.HCl salt) 3428, 2931, 1630, 1464, 1374, 1249, 1080, 1024 | (2.HCl salt); CD$_3$OD 1.02 (3H, m), 1.42(3H, m), 1.46(2H, m), 1.71–1.97(4H, m), 2.19(2H, m), 2.24(6H, s), 2.29(6H, s), 2.87(3H, s), 3.06(4H, m), 3.66(2H, m), 4.12& 4.60(1H, each m), 4.79(1H, m) |
| 25 | (structure with morpholinoethyl piperidine) | white powder (3.HCl salt) (Et$_2$O/MeOH) 266–268° C. | (3.HCl salt) 3417, 2942, 2537, 1630, 1454, 1417, 1249, 1101 | 1.43(3H, m), 1.54–2.19(6H, m), 2.07(6H, s), 2.19(6H, s), 2.46&2.52 (8H, each m), 2.98(2H, m), 3.45(2H, brs), 3.71(4H, m), 3.71&4.52 (1H, each m), 4.55(1H, m) |
| 26 | (structure with phenylcyclopropylmethyl piperidine) | white powder (2.HCl salt) (Et$_2$O/MeOH) 195–197° C. | (2.HCl salt) 3430, 2938, 1636, 1499, 1463, 1414, 1249, 1096, 700 | 0.81(1H, m), 0.96(1H, m), 1.22(1H, m), 1.43(3H, m), 1.55–2.39(8H, m), 2.07(6H, s), 2.16&2.18(6H, each s), 2.52(1H, m), 2.78&2.83 (3H, each s), 3.06(2H, m), 3.44(2H, brs), 3.71&4.53(1H, each m), 4.54(1H, m), 7.03(2H, m), 7.23(1H, m), 7.26(2H, m) |
| 27 | (structure with N-methyl-N-phenyl acetamide piperidine) | white powder (2.HCl salt) (Et$_2$O/MeOH) 205–208° C. | (2.HCl salt) 3436, 2938, 1653, 1496, 1462, 1414, 1368, 1248, 1071, 700 | 1.40(3H, d, J=6.5Hz), 1.41–2.17(6H, m), 2.08&2.17&2.21(12H, each s), 2.84&2.88(3H, each s), 2.92(4H, m), 3.28(3H, s), 3.46(2H, brs), 3.59&4.45(1H, each m), 4.54(1H, m), 7.18(2H, d, J= 7.6Hz), 7.31–7.44(3H, m) |

TABLE 5-continued
| No. | Chemical Structure | Properties | IR (KBr) cm$^{-1}$ | $^1$H-NMR (CDCl$_3$) |
|---|---|---|---|---|
| 28 | 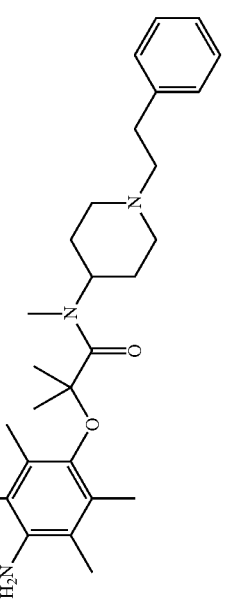 | white powder (2.HCl salt) (Et$_2$O/MeOH) 214–216° C. | (2.HCl salt) 3405, 2940, 2554, 1625, 1463, 1402, 1250, 1145, 1092, 752, 702 | 1.41(6H, s), 1.67–2.30(4H, m), 2.07&2.08&2.11&2.13(12H, each s), 2.19(2H, m), 2.58(2H, m), 2.80(2H, m), 2.90&3.35(3H, each s), 3.09(2H, m), 3.46(2H, brs), 4.54&4.86(1H, each m), 7.17–7.31(5H, m), |
| 29 | 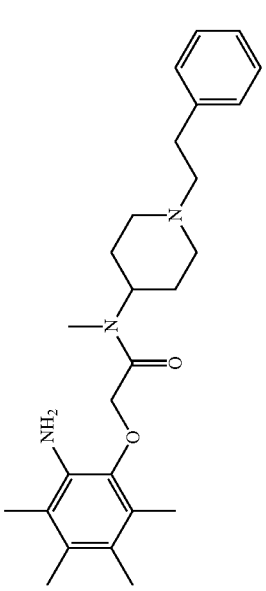 | white powder (2.HCl salt) (Et$_2$O/MeOH) 245–247° C. | (2.HCl salt) 3410, 2928, 2634 1638, 1603, 1496 1462, 1415, 1323 1250, 1102, 703 | (2.HCl salt: CD$_3$OD) 1.89–2.27(4H, m), 2.23&2.25&2.31&2.34(12H, each s), 2.87&2.92(3H, each s), 3.06–3.40(6H, m), 3.69–3.79(2H, m), 3.85&4.66(1H, m), 4.88&5.00(2H, each s), 7.31(5H, m) |

TABLE 6

| No. | Chemical Structure | Properties | IR (KBr) cm⁻¹ | ¹H-NMR (CDCl₃) |
|---|---|---|---|---|
| 30 | (structure with NH₂-trimethylphenoxy-acetyl-N-methyl-piperidine-CH₂-C(O)-phenyl) | pale yellow powder (2·HCl salt) (Et₂O/MeOH) 169–171° C. | (2·HCl salt) 3435, 2934, 2618 1694, 1639, 1598 1451, 1232, 1102 757 | 1.44–1.70(2H, m), 1.81–2.34(4H, m), 2.10(3H, s), 2.13(3H, s), 2.17(3H, s), 2.22&2.23(3H, each s), 2.77&2.92(3H, each s), 3.10 (2H, m), 3.37&4.58(1H, m), 3.82&3.85(2H, each s), 4.16(2H, brs), 4.47&4.51(2H, each s), 7.46(2H, t), 7.58(1H, t), 7.98(2H, d) |
| 31 | (structure with NH₂-trimethylphenoxy-acetyl-N-methyl-piperidine-phenoxy-phenyl) | white powder (2·HCl salt) (Et₂O/MeOH) 164–166° C. | (2·HCl salt) 3396, 2888, 2814 1641, 1588, 1508 1490, 1247, 1173 1098 | 1.72–2.09(4H, m), 2.11(3H, s), 2.14(3H, s), 2.18(3H, s), 2.23 (3H, s), 2.70&2.85(2H, m), 2.79&2.95(3H, each s), 3.49&4.69(1H, m), 3.66(2H, m), 4.19(2H, brs), 4.50&4.54(2H, each s), 6.88–7.08 (6H, m), 7.24–7.33(3H, m) |
| 32 | (structure with NH₂-trimethylphenoxy-acetyl-N-methyl-piperidine-phenyl-CH₂-(4-F-phenyl)) | pale yellow powder (2·HCl salt) (Et₂O/MeOH) 165–167° C. | (2·HCl salt) 3410, 2916, 2614 1639, 1508, 1414 1323, 1221, 1158 820 | 1.69–2.07(4H, m), 2.10(3H, s), 2.14(3H, s), 2.17(3H, s), 2.23 (3H, s), 2.68&2.83(2H, m), 2.77&2.92(3H, each s), 3.49&4.68(1H, m), 3.70(2H, m), 3.87(2H, s), 4.20(2H, brs), 4.49&4.53(2H, each s), 6.82–6.92(2H, m), 6.95(2H, t), 7.05(2H, d), 7.08–7.16(2H, m) |

TABLE 6-continued

| No. | Chemical Structure | Properties | IR (KBr) cm$^{-1}$ | $^1$H-NMR (CDCl$_3$) |
|---|---|---|---|---|
| 33 | (3-amino-2,4,6-trimethylphenoxy-acetyl-N-methyl-4-(1-benzoylpiperidinyl))amide | white powder (HCl salt) (Et$_2$O/MeOH) 171–174° C. | (HCl salt) 3423, 2934, 2577, 1626, 1518, 1447, 1318, 1279, 1250, 1107, 1025, 711 | 2.HCl salt): CD$_3$OD 1.81(4H, m), 2.26&2.29&2.32(12H, each s), 2.90&2.92(3H, each s), 2.91&3.25&3.82(4H, each m), 4.50&4.59(2H, each s), 4.75(1H, m), 7.46(5H, m), |
| 34 | (3-amino-2,4,6-trimethylphenoxy-acetyl-N-methyl-4-(1-(4-cyanobenzyl)piperidinyl))amide | white powder (2.HCl salt) (Et$_2$O/MeOH) 203–205° C. | (2.HCl salt) 3406, 2936, 1637, 1460, 1418, 1322, 1305, 1249, 1096, 1031, 944, 827 | 1.59–2.22(6H, m), 2.09&2.13&2.18(12H, each s), 2.90(2H, s), 2.88&2.92(3H, each m), 3.54(4H, brs), 3.67&4.55(1H, each m), 4.34&4.37(2H, each s), 7.43(2H, m), 7.60(2H, m), |
| 35 | (3-amino-2,4,6-trimethylphenoxy-acetyl-N-methyl-4-(1-phenethylpiperidinyl))amide | white powder (2.HCl salt) (Et$_2$O/MeOH) 157–158° C. | (2.HCl salt) 3421, 2940, 1638, 1492, 1457, 1420, 1312, 1248, 1099, 1032, 703 | 1.69–2.23(4H, m), 2.09&2.14&2.18(12H, each s), 2.60(2H, m), 2.79(2H, m), 2.87&2.92(3H, each s), 3.08(2H, m), 3.49(2H, brs), 3.66&4.58(1H, each m), 4.35&4.38(2H, each s), 7.18–7.31(5H, m) |

TABLE 7

| No. | Chemical Structure | Properties | IR (KBr) cm⁻¹ | ¹H-NMR (CDCl₃) |
|---|---|---|---|---|
| 36 | 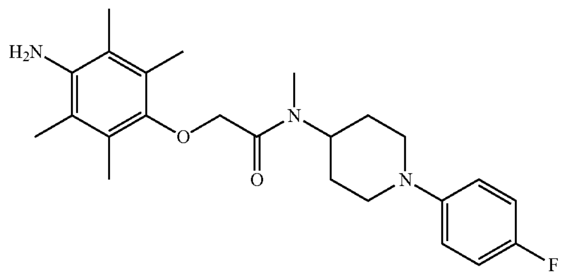 | white powder (2.HCl salt) (Et₂O/MeOH) 198–200° C. | (2.HCl salt) 3454, 2950, 2359, 1655, 1514, 1492, 1414, 1291, 1238, 1134, 1101 | 1.70–2.09(4H, m), 2.11(3H, s), 2.16(3H, s), 2.17&2.21(3H, each s), 2.68–2.87(2H, m), 2.89&2.96(3H, each s), 3.37(2H, brs), 3.60 (2H, m), 3.98&4.54–4.68(1H, m), 4.59&4.64(2H, each s), 6.56&6.61(1H, each s), 6.83–7.00(4H, m) |
| 37 | 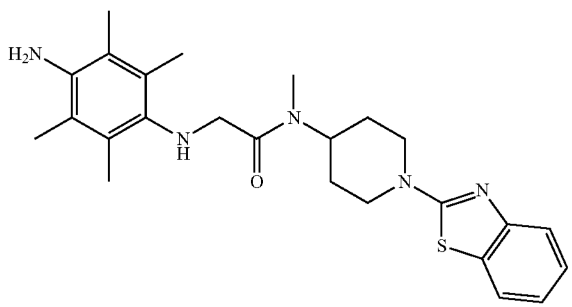 | white powder (2.HCl salt) (Et₂O/MeOH) 190–194° C. | (2.HCl salt) 3424, 2929, 1624, 1540, 1468, 1412, 1262, 1126, 1095, 1018, 762 | (2.HCl salt); DMSO 1.65–1.87(4H, m), 2.17(6H, s), 2.22(3H, s), 2.24(3H, s), 2.77 & 2.80(3H, each s), 3.30(2H, s), 3.96(2H, s), 4.13(2H, m), 4.59 (1H, m), 7.10(1H, dd), 7.30(1H, dd), 7.47(1H, d), 7.78(1H, d) |
| 38 | 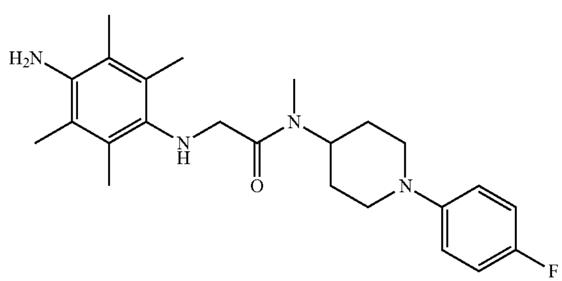 | pale yellow foam (2.HCl salt) (Et₂O/MeOH) 231–235° C. | (2.HCl salt) 3420, 1651, 1511, 1451, 1407, 1237, 1166, 1101, 1012, 844 | 1.67–2.04(4H, m), 2.13(6H, s), 2.29(6H, s), 2.65&2.82(2H, each m), 2.77&2.92(3H, each s), 3.46(2H, m), 3.61&3.66(2H, each s), 4.70(1H, m), 6.88–6.98(4H, m) |

TABLE 7-continued

| No. | Chemical Structure | Properties | IR (KBr) cm⁻¹ | ¹H-NMR (CDCl₃) |
|---|---|---|---|---|
| 39 | (structure: 3-amino-2,4,6-trimethylphenyl amide of N-methyl-N-[1-(4-fluorophenyl)piperidin-4-yl]glycine) | white powder (2.HCl salt) (Et₂O/MeOH) 193–195° C. | (2.HCl salt) 3418, 2846, 2590 1638, 1575, 1513 1488, 1409, 1358 1238, 1104 | 1.63–2.07(4H, m), 2.10&2.12&2.19&2.25&2.26(9H, each s), 2.58–2.86(2H, m), 2.78&2.92(3H, each s), 3.38–3.55&4.65(1H, m), 3.48(2H, brs), 3.60(2H, m), 3.72&3.76(2H, each s), 4.53(1H, brs), 6.68&6.75(1H, each s), 6.84–7.00(4H, m) |
| 40 | (structure: 4-amino-2,3,5,6-tetramethylphenyl amide of N-methyl-N-[1-(4-phenoxyphenyl)piperidin-4-yl]alanine) | white powder (2.HCl salt) (Et₂O/MeOH) 197–200° C. | (2.HCl salt) 3365, 2928, 2470 1638, 1588, 1507 1488, 1248, 1112, 1074 | 1.23&1.32(3H, each d), 1.41–1.98(4H, m), 2.10(3H, s), 2.11(3H, s), 2.24(3H, s), 2.27(3H, s), 2.55–2.88(2H, m), 2.71&2.79(3H, each s), 3.29–3.68(4H, m), 3.45&4.62(1H, m), 6.84–7.33(9H, m) |
| 41 | (structure: 4-amino-2,3,5,6-tetramethylphenyl amide of N-methyl-N-[1-(4-biphenyl)piperidin-4-yl]alanine) | white powder (2.HCl salt) (Et₂O/MeOH) 175–177° C. | (2.HCl salt) 3384, 2922, 2478, 1638, 1573, 1486, 1452, 1393, 1364, 1335, 1075 | (2.HCl salt)CD₃OD 1.23&1.33(3H, each d), 1.45–1.99(4H, m), 2.10(3H, s), 2.11(3H, s), 2.24(3H, s), 2.27(3H, s), 2.23–2.95(2H, m), 2.70&2.79(3H, each s), 3.30–3.85(4H, m), 3.47&4.66(1H, m), 3.97(1H, m), 6.92–7.03 (2H, m), 7.24–7.34(3H, m), 7.47–7.59(3H, m) |

The effect of aminophenoxyacetamide derivatives of the present invention represented by the formula (I) was evaluated by the following biological testing methods.

Test 1: Evaluation for neuroprotective effect against glutamate induced neurodegeneration, by comparing the administration of the test compound prior to the glutamate addition with the simultaneous administration of the test compound along with the glutamate.

Test 2: Evaluation for antagonism against cell death by treatment of various kinds of receptor inhibitor and MTA [5-deoxy-5-methyl-thioadenosine].

Test 3: Evaluation for CalbindinD-28k production increasing effect.

Test 4: Evaluation for neuroprotective inhibiting effect by antisense oligonucleotide.

Test 5: Evaluation for cerebral edema suppressing effect.

By using of the above-mentioned biological tests, the selection of the compounds having neuroprotective effect by activating the receptor of FGF, due to the introduction of the CalbindinD-28k, one of $Ca^{2+}$-binding proteins, was performed by combining all the Test 1 to 4, by combining Test 1 and 2, by combining Test 1, 2 and 3, or by combining Test 1, 3,and 4, respectively.

The following are the detailed description of the test methods.

Biological Test 1

Evaluation for Neuroprotective Effect Against Glutamate Induced Neuronal Cell Death Primary cultures were prepared from cerebral cortices of fetal Wistar rats (E18) according to the modified method of Mattson and Kater [M. P. Mattson, Brain Res. Rev., 13, 179 (1988)]. After papain-dissociation, neurons were seeded on poly-L-lysine coated 96 wells plates (Sumitomo Bakelite Co., Ltd.) at density of $5 \times 10^4$ cells/well and cultivated in 100 µl of DMEM medium (Dulbecco's modified Eagle medium (Gibco) supplemented with 10 mM $NaHCO_3$, 15 mM KCl, 1 mM sodium pyruvate, and 10% (vol/vol) horse serum). Cultures were maintained at 37 C. in a 90% air/10% $CO_2$ humidified incubator. Glutamate was added to the culture at day 4 to the final concentration of 1 mM. Cell survival was then determined 1 day later by using 3-(4,5-dimethyl-2-thiazolyl)-2,5-diphenyl-2H tetrazolium bromide (MTT). MTT was dissolved in phosphate buffered saline (PBS, pH 7.4) at 5 mg/ml and filtered to sterilize and remove a small amount of insoluble residue present in some batches of MTT, and added to the cultures at a final concentration of 0.5 mg/ml. Six hours after incubation, culture medium was discarded to stop the reaction. Dimethyl sulfoxide was added to all wells and mixed thoroughly to dissolve the dark blue crystals. After a few minutes at room temperature, the plates were read by using Micro ELISA Reader at a test wavelength of 570 nm and a reference wavelength of 650 nm.

The test compounds (1 µM) was added 24 hrs prior to glutamate treatment and simultaneously with glutamate.

The effect of the test compounds was determined as the survival rate of living cells (%) according to the following equation:

Survival rate of living cells (%) =[(test compound group—glutamic acid treated group)÷(control group—glutamic acid treated group)]×100

That is, the survival rate of living cells after incubation of the control group was converted to 100%, and the survival rate of living cells of the tested compounds was calculated.

Biological Test 2

Evaluation for Antagonism Against Neuronal Cell Death by Treatment of Various Kinds of Receptor Inhibitor of Physiological Active Substances and MTA This biological test is performed to determine whether the neuroprotective effect of the test compounds is due to the activation of receptors of physiological active substances or not, by using antagonistic test for neutralizing antibody and Inhibitor for FGF, NT-3, NT-4/5, BDNF, IGF-I/II, NGF, PDGF and estrogen, respectively.

MTA (5-deoxy-5-methylthioadenosine) specifically inhibits the autophosphorylation of FGF receptor in the living cells [P. A. Mather, J. Bio. Chem., 268, 4244 (1993)]. Therefore, the neuroprotective effect of the test compounds is inhibited by treatment of MTA, this effect is depended by the signal transfer effect through the phosphorylation of FGF receptor.

The inhibitors of the various kinds of receptor were dissolved in the optimum concentration, and MTA was dissolved in the concentration of 7.5 mM, just before the using. 30 minutes before the treatment of the test compounds, the optimum concentration of each inhibitors or 0.75 mM of MTA was added, and the neuroprotective effect of the test compounds was determined by mean of MTT method.

The results of each Biological Test 1 and 2 were shown in the following Table 8.

TABLE 8

| Compound No. | Survival Rate (%) (Compound: 1 µl) | Survival Rate (%) (Compound: 1 µl & MTA treatment) |
|---|---|---|
| 6 | 54 | 25 |
| 7 | 76 | 32 |
| 8 | 78 | 24 |
| 9 | 104 | 5 |
| 10 | 86 | 31 |
| 11 | 74 | 56 |
| 12 | 54 | 33 |
| 13 | 65 | 13 |
| 16 | 101 | 33 |
| 17 | 85 | 55 |
| 18 | 91 | 57 |
| 19 | 96 | 28 |
| 22 | 79 | 32 |
| 24 | 61 | 22 |
| 25 | 87 | 16 |
| 28 | 103 | 46 |
| 32 | 73 | 34 |
| 33 | 120 | 46 |
| 34 | 74 | 21 |
| 36 | 97 | 25 |
| 37 | 95 | 20 |
| 38 | 124 | 19 |
| 39 | 94 | 28 |

Biological Test 3

Evaluation for CalbindinD-28k Inducing Effect

Primary cultures were prepared from cerebral cortices of fetal Wistar rats (E18) according to the modified method of Mattson and Kater[M. P. Mattson, Brain Res. Rev., 13, 179 (1988)]. After papain-dissociation, neurons were seeded on poly-L-lysine coated 6 wells plates (Falcon) at density of 5500 cells/$mm^2$ and cultivated in 2 ml of DMEM medium.

Test compounds were added 5 days after initiation of the incubation, and after 7 days of incubation, the protein was extracted with homogenized buffer solution [containing 20 mm of Tris-HCl (pH=7.4), 1 mM of EDTA, and 0.1 mM of phenylmethyl-sulfonyl fluoride].

The effect of the test compounds was determined by the western blot technique using polyclonal anti CalbindinD-28k Swant (Swant Co., Ltd.) as antibody.

Table 9 shows the test results. In the table, the amount of induced CalbindinD-28k of the control group (none-treated group) was 4indicated as 100 percents.

TABLE 9

| Compound No. | Amount of induced CalbindineD-28k (% vs. control) (Compound: 1 μM) |
|---|---|
| 6 | 163 |
| Control | 100 |

Biological Test 4

Evaluation for Neuroprotective Inhibiting Effect by Antisense Oligonucleotide

It is necessary to produce the protective protein for the signal transfer action of cells through the phosphorylation of FGF receptor for the neuroprotective effect of the test compounds, and the CalbindinD-28k is one of that protective proteins having $Ca^{2+}$ buffering function. Therefore, the following test determined whether CalbindinD-28k is concerned in the neuroprotective effect of the test compounds by using an antisense oligonucleotide.

Primary cultures were prepared from cerebral cortices of fetal Wistar rats (E18). After papain-dissociation, neurons were seeded on poly-L-lysine coated 96 wells plates (Sumitomo Bakelite Co., Ltd.) at density of $4 \times 10^4$ cells/well and cultivated in 100 μl of DMEM medium.

From 2 days after the incubation to 8 days, 100 μl of Neurobasal medium/2% B-27 Supplement and 5 μM of three kinds of antisense oligonucleotides were added respectively, on every 24 hours. 7 days after incubation, 1 μM and 10 μM of the test compounds were added, and 8 days after incubation, 300 μM of glutamic acid was added. Cell survival was then determined 1 day later by using MTT. Six hours after incubation, culture medium was discarded to stop the reaction. Dimethyl sulfoxide was added to all wells and mixed thoroughly to dissolve the dark blue crystals. After a few minutes at room temperature, the plates were read by using Micro ELISA Reader at a test wavelength of 570 nm and a reference wavelength of 650 nm.

The effect of the test compounds was determined as the survival rate of living cells (%) according to the equation as indicated in the Biological Test 1: That is, the survival rate of living cells after incubation of the control group was converted to 100%, and the survival rate of living cells of the tested compounds was calculated.

The sequences of the antisense oligonucleotides to be used in this test are following.
calbindin antisense 1: 5-TGA CTG CAG GTG GGA TTC TGC-3
calbindin antisense 2: 5-ACC GTC GAA ATG AAG CCA GA-3
calbindin antisense 3: 5-CGT ATC ATC CAC GGT CTT GTT-3

Table 10 shows the test results.

TABLE 10

| Test Compound | Survival Rate (%) [antisense (−)] | Survival Rate (%) [antisense (+): 5 μM] |
|---|---|---|
| BFGF (1 ng) | 71 | 8 |
| BFGF (10 ng) | 101 | 35 |
| No. 6 (0.1 μM) | 103 | 30 |
| No. 6 (1 μM) | 108 | 34 |
| No. 38 (0.1 μM) | 100 | 28 |
| No. 38 (1 μM) | 106 | 33 |

Biological Test 5

Evaluation for Cerebral Edema Suppressing Effect

Adult male Wistar rats weighing 210–230 g were used in the present study and housed in an artificially controlled environment with 12-hour light/dark cycle. Animals were anesthetized with pentobarbital sodium (50 mg/kg of body weight, i.p., Nembutal, Dinabbott, Japan) and placed in a stereotaxic apparatus. The skull was exposed and a hole was made on the parietal bone; 1.5 mm posterior and 0.8 mm lateral to the bregma. All procedures were performed under a surgery microscope to avoid excess irritation to the meninges and the underlying brain. A brass screw with a blunt tip (1.0 mm in diameter and 3.0 mm in length, Biomedica, Japan) was inset in the hole. The screw tip protruding intracranially was approximately 2.5 mm, which stuck into the parietal part of the right cerebrum through the meninges. In sham-operated rats, scalp was closed without attaching a screw to the hole. After surgery, all rats were kept in their original dens until sacrifice. Rats were allowed to feed chow and water ad libitum.

Under anesthesia the rat cerebral hemispheres of the target were processed for water content on post-TBI day 6 (n=6). The cerebral hemispheres dissected out were weighed, dried for 24 hours at 110 degree (Celsius) and then weighed again. The subtracted amount of the wet and dry weights was regarded as tissue water of the target, and utilized for the analysis of the cerebral edema.

The water content was calculated by using the following formula:

Water content (%) =[(wet weight of hemisphere—dry weight of hemisphere)/wet weight of hemisphere]×100

The test compounds were intravenously administered just after the operation via tail vein of the rats.

Table 11 shows the test results.

TABLE 11

| Compound No. (administration amount) | Cerebral edema suppressing rate (%) |
|---|---|
| 6 (3 mg/kg) | 24.9 |
| 8 (1 mg/kg) | 14.0 |
| 12 (3 mg/kg) | 14.7 |
| 13 (3 mg/kg) | 13.1 |
| 14 (1 mg/kg) | 18.7 |
| 15 (1 mg/kg) | 14.7 |
| 18 (1 mg/kg) | 22.1 |
| 24 (1 mg/kg) | 10.6 |
| 25 (1 mg/kg) | 19.1 |
| 26 (3 mg/kg) | 11.9 |
| 27 (3 mg/kg) | 11.8 |
| 29 (1 mg/kg) | 13.8 |

INDUSTRIAL APPLICABILITY

As described above, the present invention provides lower molecular compounds, especially aminophenoxyacetamide derivatives of the formula (I), which induce the CalbindinD-28k, one of $Ca^{2+}$-binding proteins, and can be easily administrated. Since the induction of CalbindinD-28k caused by the administration of the compound provided by the present invention cause neuroprotective effect and cerebral functional and organic disorder improving and treating effect, it can be understood that the agent of the present invention is highly applicable in pharmaceutical field.

---

The invention claimed is:

1. An aminophenoxyacetamide derivative represented by the following formula (I):

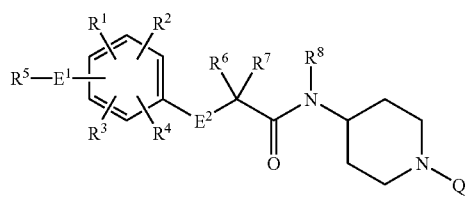

wherein:
- $R^1$, $R^2$, $R^3$ and $R^4$ are, independent from each other, hydrogen atom or lower alkyl group;
- $R^5$ $R^6$ $R^7$ and $R^8$ are, independent from each other, hydrogen atom or lower alkyl group;
- $E^1$ is group —$NR^9$— (in which, $R^9$ is hydrogen atom or lower alkyl group);
- $E^2$ is oxygen atom or group —$NR^{10}$— (in which, $R^{10}$ is hydrogen atom or lower alkyl group which may be substituted);
- Q is a group of —X—Y-Q', wherein X is a connecting bond, lower alkyl group, lower alkenyl group, or lower alkenyl group; Y is a connecting bond, or a group selected from the groups consisting of C=O, C(=O)NH, NHC(=O), —O—, —S—, CH(OH), —O—CH(OH)— and —O—CH$_2$—CH(OH)—, in which hydrogen atom of amido group may be substituted with lower alkyl group; and Q' is hydrogen atom or a cyclic group selected from the group consisting of phenyl group, pyridily group, quinolyl group, isoquinolyl group, benzothiazole group, benzimidazole group, morpholinyl group, and cyclic hydrocarbon group, wherein one or more of the hydrogen atoms in the cyclic group of Q' may be substituted;
- either in the case that $E^2$ is the group —$NR^{10}$— then X and Y are both connecting bond and Q' is not hydrogen atom; or in the case that $E^2$ is the group —O— then all of the groups $R^1$, $R^2$, $R^3$ and $R^4$ are methyl group; or a pharmaceutically acceptable salt thereof.

2. The aminophenoxyacetamide derivative of formula (I) claimed in claim 1, wherein X and Y are both connecting bond; or pharmaceutically acceptable salts thereof.

3. The aminophenoxyacetamide derivative of formula (I) claimed in claim 1, wherein one of X and Y is other than connecting bond and $E^2$ is the group —O— and all of the groups of $R^1$, $R^2$, $R^3$ and $R^4$ are other than hydrogen atom, wherein X, Y, $R^1$, $R^2$, $R^3$ and $R^4$ are the same as defined above in claim 1; or pharmaceutically acceptable salts thereof.

4. A composition comprising an aminophenoxyacetamide derivative or a pharmaceutically acceptable salt thereof represented by the formula (I) in claim 1 as an active ingredient.

5. A composition comprising an aminophenoxyacetamide derivative or a pharmaceutically acceptable salt thereof represented by the formula (I) in claim 2 as an active ingredient.

6. A composition comprising an aminophenoxyacetamide derivative or a pharmaceutically acceptable salt thereof represented by the formula (I) in claim 3 as an active ingredient.

7. An aminophenoxyacetamide derivative represented by the following formula (I):

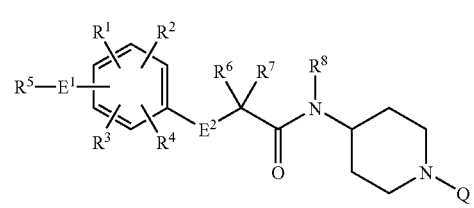

wherein:
- $R^1$, $R^2$, $R^3$ and $R^4$ are, independent from each other, hydrogen atom or lower alkyl group;
- $R^5$ $R^6$ $R^7$ and $R^8$ are, independent from each other, hydrogen atom or lower alkyl group;
- $E^1$ is group —$NR^9$— (in which, $R^9$ is hydrogen atom or lower alkyl group);
- $E^2$ is oxygen atom or group —$NR^{10}$— (in which, $R^{10}$ is hydrogen atom or lower alkyl group which may be substituted);
- Q is a group of —X—Y-Q', wherein X is a connecting bond, lower alkyl group, lower alkenyl group, or lower alkenyl group; Y is a connecting bond, or a group selected from the groups consisting of C=O, C(=O)NH, NHC(=O), —O—, —S—, CH(OH), —O—CH(OH)— and —O—CH$_2$—CH(OH)—, in which hydrogen atom of amido group may be substituted with lower alkyl group; and Q' is hydrogen atom or a cyclic group selected from the group consisting of phenyl group, pyridily group, ciuinolyl group, isociuinolyl group, benzothiazole group, benzimidazole group, morpholinyl group, and cyclic hydrocarbon group, wherein one or more of the hydrogen atoms in the cyclic group of Q' may be substituted;
- either in the case that $E^2$ is the group —NR— then X and Y are both connecting bond and Q' is not hydrogen atom; or in the case that $E^2$ is the group —O— then all of the groups $R^1$, $R^2$, $R^3$ and $R^4$ are methyl group; or a pharmaceutically acceptable salt thereof,
- where Q' is a cyclic hydrocarbon group and said cyclic hydrocarbon group is cyclopropyl, cyclobutyl, cyclopentyl, or cyclohexyl.

8. An aminophenoxyacetamide derivative represented by the following formula (I):

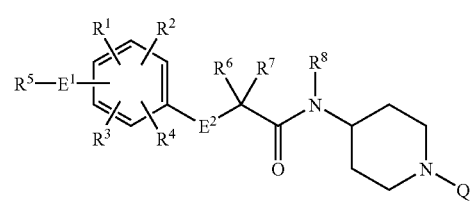

wherein:
- $R^1$, $R^2$, $R^3$ and $R^4$ are, independent from each other, hydrogen atom or lower alkyl group;
- $R^5$ $R^6$ $R^7$ and $R^8$ are, independent from each other, hydrogen atom or lower alkyl group;
- $E^1$ is group —$NR^9$— (in which, $R^9$ is hydrogen atom or lower alkyl group); $E^2$ is oxygen atom or group —NR$^{10}$— (in which, R$^{10}$ is hydrogen atom or lower alkyl group which may be substituted);

Q is a group of —X—Y-Q', wherein X is a connecting bond, lower alkyl group, lower alkenyl group, or lower alkenyl group; Y is a connecting bond, or a group selected from the groups consisting of C=O, C(=O)NH, NHC(=O), —O—, —S—, CH(OH), —O—CH(OH)— and —O—CH$_2$—CH(OH)—, in which hydrogen atom of amido group may be substituted with lower alkyl group; and Q' is hydrogen atom or a cyclic group selected from the group consisting of phenyl group, pyridily group, ciuinolyl group, isociuinolyl group, benzothiazole group, benzimidazole group, morpholinyl group, and cyclic hydrocarbon group, wherein one or more of the hydrogen atoms in the cyclic group of Q' may be substituted;

either in the case that E$^2$ is the group —NR$^{10}$— then X and Y are both connecting bond and Q' is not hydrogen atom; or in the case that E$^2$ is the group —O— then all of the groups R$^1$ R$^2$, R$^3$ and R$^4$ are methyl group; or a pharmaceutically acceptable salt thereof, wherein Q' is an unsaturated or saturated heterocyclic group and said unsaturated or saturated heterocyclic group is morpholinyl.

* * * * *

SEQUENCE LISTING

```
<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Antisense DNA to act as a blocker for
      production of calbindin-D 28K
<300> PUBLICATION INFORMATION:
<302> TITLE: Induction of calbindin-D 28K gene and protein expression by
      physiological stimuli but not in calcium-mediated degeneration
      in rat PC12 pheochromocytoma cells
<303> JOURNAL: FEBS Letters
<304> VOLUME: 352
<305> ISSUE: 1
<306> PAGES: 53-57
<307> DATE: 1994-08-29

<400> SEQUENCE: 1
tgactgcagg tgggattctg c                                            21

<210> SEQ ID NO 2
<211> LENGTH: 20
<212> TYPE: DNA
<213> ORGANISM: Artificial Sequence
<220> FEATURE:
<223> OTHER INFORMATION: Antisense DNA to act as a blocker for
      production of calbindin-D 28K
<300> PUBLICATION INFORMATION:
<302> TITLE: Induction of calbindin-D 28K gene and protein expression by
      physiological stimuli but not in calcium-mediated degeneration
      in rat PC12 pheochromocytoma cells
<303> JOURNAL: FEBS Letters
<304> VOLUME: 352
<305> ISSUE: 1
<306> PAGES: 53-57
<307> DATE: 1994-08-29

<400> SEQUENCE: 2
accgtcgaaa tgaagccaga                                              20

<210> SEQ ID NO 3
<211> LENGTH: 21
<212> TYPE: DNA
<213> ORGANISM: Artificial Sequence
<220> FEATURE:
<223> OTHER INFORMATION: Antisense DNA to act as a blocker for
      production of calbindin-D 28K
<300> PUBLICATION INFORMATION:
<302> TITLE: Induction of calbindin-D 28K gene and protein expression by
      physiological stimuli but not in calcium-mediated degeneration
      in rat PC12 pheochromocytoma cells
<303> JOURNAL: FEBS Letters
<304> VOLUME: 352
<305> ISSUE: 1
<306> PAGES: 53-57
<307> DATE: 1994-08-29

<400> SEQUENCE: 3
cgtatcatcc acggtcttgt t                                            21
```